US006171821B1

(12) United States Patent
Korneluk et al.

(10) Patent No.: US 6,171,821 B1
(45) Date of Patent: *Jan. 9, 2001

(54) XIAP IRES AND USES THEREOF

(75) Inventors: Robert G. Korneluk; Martin Holcik; Peter Liston, all of Ottawa (CA)

(73) Assignee: Apoptogen, Inc., Ottawa (CA)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/332,319

(22) Filed: Jun. 14, 1999

Related U.S. Application Data

(63) Continuation-in-part of application No. 09/121,979, filed on Jul. 24, 1998.

(51) Int. Cl.[7] .......................... C12P 21/06; C12P 19/34; C12Q 1/68; C12N 15/00; A61K 48/00
(52) U.S. Cl. .......................... 435/69.1; 435/6; 435/91.1; 435/320.1; 435/325; 435/375; 536/24.1; 514/44
(58) Field of Search .................................. 536/23.1, 24.5, 536/24.3, 24.33; 435/6, 91.1, 93.1, 320.1, 69.1

(56) References Cited

U.S. PATENT DOCUMENTS 5,358,856 * 10/1994 Baltimore et al. ................... 435/69.1

FOREIGN PATENT DOCUMENTS

| WO 96/11211 | 4/1996 | (WO) . |
|---|---|---|
| WO 97/06182 | 2/1997 | (WO) . |
| WO 97/06255 | 2/1997 | (WO) . |
| WO 97/26331 | 7/1997 | (WO) . |
| WO 98/21321 | 5/1998 | (WO) . |
| WO 98/22131 | 5/1998 | (WO) . |
| WO 98/35693 | 8/1998 | (WO) . |

OTHER PUBLICATIONS

Farahani et al., "Mus Musculus X–linked Inhibitor of Apoptosis (Miap–3) mRNA, Complete CDs," Abstract, Genomics (1997) vol. 42, No. 5, 514–518.
Gurtu et al., "IRES Bicistronic Expression Vectors for Efficient Creation of Stable Mammalian Cell Lines," Biochemical and Biophysical Research Communications 229:295–298 (1996).
Holcik et al., "A New Internal–ribosome–entry–site Motif Potentiates XIAP–mediated Cytoprotection," Nature Cell Biology 1:190–192 (1999).
Le et al., "A Common RNA Structural Motif Involved in the Internal Initiation of Translation of Cellular mRNAs," Nucleic Acids Research 25:362–369 (1997).
Liston et al., "Human X–linked Inhibitor of Apoptosis Protein XIAP mRNA, Complete CDs," Abstract.
Andrea D. Branch, A good antisense molecule is hard to find, TIBS, 47–48, Feb. 1998.
Trisha Gura, Antisense Has Growing Pains, Science, pp. 575–575, Oct. 1995.
Stanley Crooke, Antisense '97: A roundtable on the state of the industry, Nature Biotechnology, p. 522, Jun. 1997.
Orkin et al., Report and recommendations of the panel to assess the NIH investment in research on gene therapy, pp. 1–23, Dec. 1995.
W. French Anderson, Human gene therapy, Nature, vol. 392, Supp, pp. 25–30, Feb. 1998.
Belsham, "Analysis of Picornavirus Internal Ribosome Entry Site Function in Vivo," In J.D. Richter (ed.), *mRNA Formation and Function*, Academic Press, New York, pp. 323–340 (1997).
Deveraux et al., "X–Linked IAP is a Direct Inhibitor of Cell–death Proteases," Nature 388:300–304 (1997).
Ehrenfeld, "Initiation of Translation by Picornavirus RNAs," In J.W.B. Hershey, M.B. Matthews and N. Sonenberg (eds.), *Translational Control*, Cold Spring Harbor Laboratory Press, Cold Spring Harbor Laboratory pp. 549–573 (1996).
Farahani et al., "Genomic Organization and Primary Characterization of miap–3: The Murine Homologue of Human X–linked IAP," Genomics 42:514–518 (1997).
Gan et al., "Functional Characterization of the Internal Ribosome Entry Site of eIF4G mRNA," J. Biol. Chem. 273:5006–5012 (1998).
Imataka et al., "A New Translational Regulator with Homology to Eukaryotic Translation Initiation Factor 4G," EMBO J. 16:817–825 (1997).
Jackson, "A Comparative View of Initiation Site Selection Mechanisms," In J.W.B. Hershey, M.B. Matthews and N. Sonenberg (eds.), *Translational Control*, Cold Spring Harbor Laboratory Press, Cold Spring Harbor Laboratory pp. 71–112 (1996).
LaCasse et al., "The Inhibitors of Apoptosis (IAPs) and Their Emerging Role in Cancer," Oncogene 17:3247–3259 (1998).
Levy–Strumpf et al., "DAP–5, A Novel Homolog of Eukaryotic Translation Initiation Factor 4G Isolated as a Putative Modulator of Gamma Interferon–Induced Programmed Cell Death," Mol. Cell. Biol. 17:1615–1625 (1997).

(List continued on next page.)

*Primary Examiner*—George C. Elliott
*Assistant Examiner*—Janet L. Epps
(74) *Attorney, Agent, or Firm*—Clark & Elbing LLP; Kristina Bierker-Brady

(57) ABSTRACT

The invention features purified nucleic acid encoding a novel internal ribosome entry site (IRES) sequence from the X-linked inhibitor of apoptosis (XIAP) gene. The invention also features methods for using the XIAP IRES to increase cap-independent translation of polypeptide coding sequences linked to the XIAP IRES, and methods for isolating compounds that modulate cap-independent translation.

29 Claims, 11 Drawing Sheets

OTHER PUBLICATIONS

Liston et al., "Genomic Characterization of the Mouse Inhibitor of Apoptosis Protein 1 and 2 Genes," Genomics 46:495–503 (1997).

Liston et al., "Suppression of Apoptosis in Mammalian Cells by NAIP and a Related Family of IAP Genes," Nature 379:349–353 (1996).

Liston et al., "Life and Death Decisions: The Role of the IAPs in Modulating Programmed Cell Death," Apoptosis 2:423–441 (1997).

Macejak et al., "Internal Initiation of Translation Mediated by the 5' Leader of a Cellular mRNA," Nature 353:90–94 (1991).

Meerovitch et al., "La Autoantigen Enhances and Corrects Aberrant Translation of Poliovirus RNA in Reticulocyte Lysate," Journal of Virology 67:3798–3807 (1993).

Nanbru et al., "Alternative Translation of the Proto–Oncogene c–myc by an Internal Ribosome Entry Site," J. Biol. Chem. 272:32061–32066 (1997).

Oh et al., "Homeotic Gene Antennapedia mRNA Contains 5'–Noncoding Sequences That Confer Translational Initiation by Internal Ribosome Binding," Genes. Dev. 6:1643–1653 (1992).

Pelletier et al., "Internal Initiation of Translation of Eukaryotic mRNA Directed By a Sequence Derived From Poliovirus RNA," Nature 334:320–325 (1988).

Rothe et al., "The TNFR2–TRAF Signaling Complex Contains Two Novel Proteins Related to Baculoviral Inhibitor of Apoptosis Proteins," Cell 83:1243–1252 (1995).

Roy et al., "The Gene for Neuronal Apoptosis Inhibitory Protein is Partially Deleted in Individuals with Spinal Muscular Atrophy," Cell 80:167–178 (1995).

Roy et al., "The c–IAP–1 and c–IAP–2 Proteins are Direct Inhibitors of Specific Caspases," EMBO J. 16:6914–6925 (1997).

Sachs et al., "Starting at the Beginning, Middle, and End: Translation Initiation in Eukaryotes," Cell 89:831–838 (1997).

Seshagiri et al., "Baculovirus Inhibitors of Apoptosis (IAPs) Block Activation of Sf–caspase–1," Proc. Natl. Acad. Sci. USA 94:13606–13611 (1997).

Stein et al., "Translational of Vascular Endothelial Growth Factor mRNA by Internal Ribosome Entry: Implications for Translation Under Hypoxia," Mol. Cell Biol. 18:3112–3119 (1998).

Stoneley et al., "C–Myc 5' Untranslated Region Contains an Internal Ribosome Entry Segment," Oncogene 16:423–428 (1998).

Takahashi et al., "A Single BIR Domain of XIAP Sufficient for Inhibiting Caspases," J. Biol. Chem. 273:7787–7789 (1998).

Trono et al., "Translation in Mammmalian Cells of a Gene Linked to the Poliovirus 5' Noncoding Region," Science 241:445–448 (1988).

Uren et al., "Cloning and Expression of Apoptosis Inhibitory Protein Homologs That Function to Inhibit Apoptosis and/or Bind Tumor Necrosis Factor Receptor–associated Factors," Proc. Natl. Acad. Sci. USA 93:4974–4978 (1996).

Vagner et al., "Alternative Translation of Human Fibroblast Growth Factor 2 mRNA Occurs by Internal Entry of Ribosomes," Mol. Cell Biol. 15:35–44 (1995).

Wagenknecht et al., "Expression and Biological Activity of X–linked Inhibitor of Apoptosis (XIAP) in Human Malignant Glioma," Cell Death and Differentiation 6:370–375 (1999).

Ye et al., "Ultrabithorax and Antennapedia 5' Untranslated Regions Promote Developmentally Regulated Internal Translation Initiation," Mol. Cell Biol. 17:1714–1721 (1997).

* cited by examiner

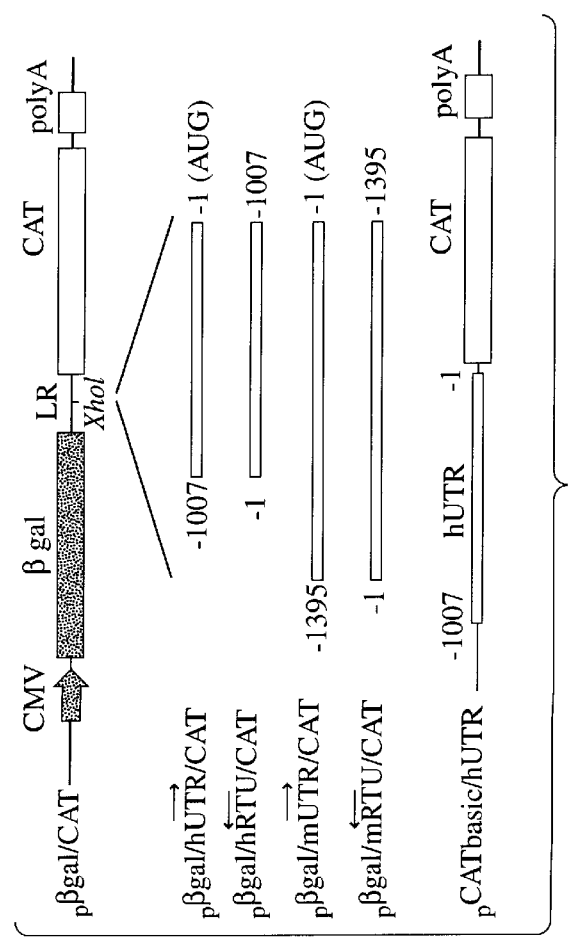
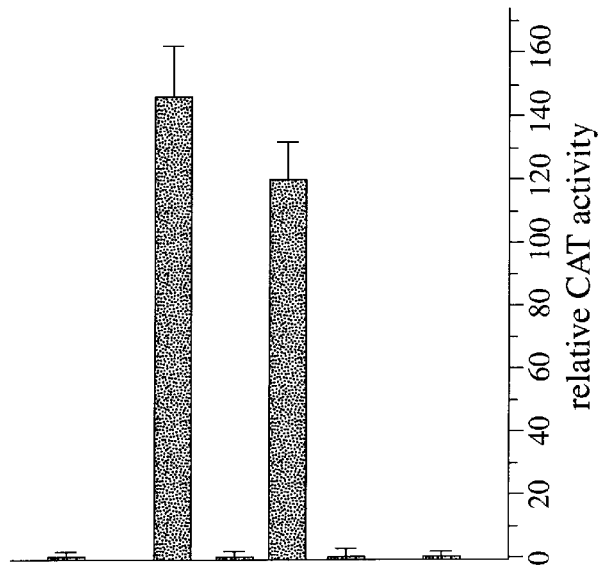
Fig. 1A
Fig. 1B

US 6,171,821 B1

XIAP IRES AND USES THEREOF

CROSS REFERENCE TO RELATED APPLICATIONS

This application is a continuation-in-part of U.S. Ser. No. 09/121,979, filed Jul. 24, 1998.

FIELD OF THE INVENTION

The field of the invention is regulation of protein translation.

BACKGROUND OF THE INVENTION

Programmed cell death plays a critical role in regulating cell turnover during embryogenesis, metamorphosis, tissue homeostasis, viral infections, and cancer. Previously, we identified and cloned three mammalian genes encoding inhibitor of apoptosis proteins (IAPs): HIAP1, HIAP2, and XIAP (Farahani, R., et al, *Genomics,* 42:514–8, 1997; Liston, P., ct al., *Genomics,* 46:495–503, 1997a; Liston, P., et al., *Nature,* 379:349–53, 1996). While the IAP genes were initially discovered in baculoviruses, their homologues have since been identified in other viruses, insects, birds, and mammals, suggesting a common evolutionary origin.

X-linked IAP (XIAP) is a member of the mammalian IAP gene family. The anti-apoptotic function of XIAP is executed, at least in part, by inhibition of caspase-3 and caspase-7, two principal effectors of apoptosis. Interestingly, XIAP mRNAs are present in all human and murine fetal and adult tissues examined.

Most eukaryotic mRNAs are translated primarily by ribosome scanning. First, the 40S ribosomal subunit with its associated initiation factors binds to the 5'7-methylguanosine ($m^7G$)-cap structure of the mRNA to be translated. The complex then scans in the 3' direction until an initiation codon in a favorable context is encountered, at which point protein translation is initiated. According to this model, the presence of a 5' untranslated region (UTR) with strong secondary structure and numerous initiation codons would present a significant obstacle, leading to inefficient translation by ribosome scanning. Ribosome reinitiation, shunting, and internal ribosome binding are secondary mechanisms of translation initiation that alleviate the requirement for ribosome scanning and allow translation to proceed in a cap-independent manner.

Internal ribosome entry site (IRES) elements, which were first identified in picornaviruses, are considered the paradigm for cap-independent translation. The 5' UTRs of all picornaviruses are long and mediate translational initiation by directly recruiting and binding ribosomes, thereby circumventing the initial cap-binding step.

Although IRES elements are frequently found in viral mRNAs, they are rarely found in non-viral mRNAs. To date, the non-viral mRNAs shown to contain functional IRES elements in their respective 5' UTRs include those encoding immunoglobulin heavy chain binding protein (BiP) (Macejak, D. G., et al. *Nature,* 35390–4, 1991); Drosophila Antennapedia (Oh, S. K., et al., *Genes Dev,* 6:1643–53, 1992) and Ultrabithorax (Ye, X., et al., *Mol. Cell Biol.,* 17:1714–21, 1997); fibroblast growth factor 2 (Vagner, S., et al., *Mol. Cell Biol.,* 15:35–44, 1995); initiation factor eIF4G (Gan, et al., *J. Biol. Chem.,* 273:5006–12, 1998); proto-oncogene c-myc (Nanbru, et al., *J. Biol. Chem.,* 272:32061–6, 1995; Stoneley, M., *Oncogene,* 16:423–8, 1998); and vascular endothelial growth factor (VEGF) (Stein, I., et al., *Mol. Cell Biol.,* 18:3112–9, 1998).

Cellular IRES elements have no obvious sequence or structural similarity to picornavirus IRES sequences, or to each other. Moreover, the mechanism for the regulation of IRES-directed translation is not understood. An understanding of the mechanism by which IRES elements direct cap-independent translation of cellular mRNAs and characterization of novel IRES sequences will provide new approaches for regulating the intracellular levels of both endogenously- and exogenously-encoded proteins.

SUMMARY OF THE INVENTION

XIAP protein plays a critical role in regulating programmed cell death by suppressing activation of downstream caspase-3 and caspase-7. We have identified an IRES that mediates XIAP translation. The XIAP IRES element is located within a 265 nucleotide (nt) region of the XIAP 5' untranslated region (UTR).

IRES-directed translation of XIAP is resistant to the repression of protein synthesis during serum deprivation-induced apoptosis. Furthermore, IRES-mediated translation of XIAP offers enhanced protection against apoptosis induced by serum deprivation in cultured HeLa cells. These studies demonstrate that the presence of an IRES element in mRNA allows a linked protein-encoding sequence to be selectively translated following the repression of cap-dependent translation. The XIAP IRES may be included in a recombinant transcription unit (e.g., a vector) to regulate the level of recombinant protein in a cell, particularly a cell under environmental stress. Furthermore, XIAP IRES antisense nucleic acid may be used to decrease a cell's resistance to apoptosis (e.g., a cancer cell). The XIAP IRES also may be used to identify compounds that modulate cap-independent protein translation.

In a first aspect, the invention features a purified nucleic acid comprising or encoding a XIAP IRES, wherein, if nucleotides are present 5' or 3' to the XIAP IRES, the nucleic acid comprises at least one variant nucleotide within a 500 nucleotide region 5' or 3' to the XIAP IRES. The variant nucleotide is a nucleotide that is not present at the position of the variant nucleotide in a naturally occurring XIAP gene or XIAP mRNA, relative to the position of the XIAP IRES, and the XIAP IRES increases cap-independent translation of a cistron when the XIAP IRES is located upstream from the cistron within a messenger RNA molecule. In a preferred embodiment of the first aspect of the invention, the XIAP IRES increases stress-induced cap-independent translation. The nucleic acid may be in an expression vector.

In a second, related aspect, the invention features purified nucleic acid comprising or encoding a XIAP IRES, the IRES being 5' to a coding sequence that encodes a polypeptide that is not XIAP. The nucleic acid may be in an expression vector.

In a third, related aspect, the invention features a purified nucleic acid comprising or encoding a XIAP IRES, wherein the XIAP IRES has a nucleotide sequence substantially identical to a nucleotide sequence set forth in SEQ ID NOs: 1, 2,19–30. If nucleotides are present 5' or 3' to said XIAP IRES, the nucleic acid comprises at least one variant nucleotide within a 500 nucleotide region 5' or 3' to the XIAP IRES, the variant nucleotide being a nucleotide that is not present at the position of the variant nucleotide in a naturally occurring XIAP gene or XIAP mRNA, relative to the position of the XIAP IRES.

In a preferred embodiment of the third aspect of the invention, the nucleic acid is in an expression vector, wherein the expression vector encodes a transcription unit comprising a XIAP IRES and a coding sequence for a polypeptide. In a further embodiment, the coding sequence may encode a polypeptide that is not a XIAP polypeptide. In yet another embodiment, the expression vector may be a gene therapy vector, and the gene therapy vector may have a tissue-specific promoter. In other embodiments, the polypeptide encoded by the gene therapy vector may be selected from XIAP, NAIP, TIAP, HIAP1, HIAP2, VEGF, BCL-2, BDNF, GDNF, PDGF-B, IGF-2, NGF, CTNF, NT-3, NT-4/5, EPO, insulin, TPO, p53, VIHL, XAF, BAX, BCL-$X_{L1}$, BAD, BCL-$X_S$, and caspases 1, 2, 3, 4, 5, 6, 7, 8, 9, and 10.

In a fourth aspect, the invention features a method for increasing the level of a protein in a cell, comprising introducing into a cell an expression vector comprising a promoter operably linked to a DNA sequence encoding a transcription unit. The transcription unit comprises a XIAP IRES sequence and a coding sequence for a protein, and the presence of the XIAP IRES sequence increases the level of cap-independent translation of the protein.

In various embodiments of the fourth aspect of the invention, the cell may be at risk for undergoing apoptosis, or may be undergoing apoptosis. The risk may, e.g., be due to an autoimmune disease, a degenerative disease, or an immunorejection reaction.

In other embodiments of the fourth aspect of the invention, the cell may be at risk for or undergoing a heat shock response, or may be growth-arrested or may be a cancer cell, or the cell may be under environmental stress, such as hypoxic stress, osmotic stress, oxidative stress, radiation-induced stress, or toxin-induced stress.

In yet other embodiments of the fourth aspect of the invention, the method may be used for gene therapy, or for inhibiting apoptosis in a cell in need thereof. The protein may be selected from XIAP, NAIP, TIAP, HIAP1, HIAP2, VEGF, BCL-2, BDNF, GDNF, PDGF-B, IGF-2, NGF, CTNF, NT3, NT-4/5, EPO, insulin, TPO, p53, or BCL-$X_{L1}$.

In still other embodiments of the fourth aspect of the invention, the cell may be selected from the group including but not limited to: a neuron (e.g., a dopaminergic neuron), a cardiomyocyte, a skeletal myoblast, a skeletal myofiber, a hair follicle cell, an ovarian follicle cell, a retinal photoreceptor cell an oligodendrocyte, an astrocyte, and a pancreatic islet cell.

Moreover, the method of the fourth aspect of the invention may used for methods including but not limited to reducing hypoxic stress in a tissue under hypoxic stress, wherein the protein may be VEGF or b-FGF, wherein expression of the protein is sufficient to reduce hypoxic stress in the tissue. Preferably, the tissue is cardiac tissue or brain tissue.

In addition, the method of the fourth aspect of the invention may be used for stimulating apoptosis in a cell in need thereof. The protein may be selected from the group consisting of: caspases 1–10, BAX, BAD, BCL-$X_S$, TRADD, FADD, XAF, VHL, and p53. In one preferred embodiment, the cell may be a cancer cell.

In a fifth aspect, the invention features a method for identifying a compound that modulates protein translation comprising: a) providing a reporter cistron that is under the translational regulation of a XIAP IRES (a XIAP IRES reporter cistron); b) exposing the XIAP IRES reporter cistron to a test compound; and c) determining the amount of translation from the XIAP IRES reporter cistron exposed to the compound, relative to the amount of translation from the XIAP IRES reporter cistron not exposed to the compound. A relative increase in translation from the XIAP IRES reporter cistron exposed to the compound indicates a compound that increases XIAP IRES-dependent protein translation, and a relative decrease in translation from the XIAP IRES reporter cistron exposed to the compound indicates a compound that decreases XIAP IRES-dependent protein translation.

In a preferred embodiment of the fifth aspect of the invention, the method may further include a reporter cistron that is not under the translational regulation of the XIAP IRES (an "internal control" reporter cistron), wherein: a) the amount of translation from the XIAP IRES reporter cistron exposed to the compound is normalized relative to the amount of translation of the internal control reporter cistron exposed to the compound, and b) the amount of translation from the XIAP IRES reporter cistron not exposed to the compound is normalized relative to the amount of translation of the internal control reporter cistron not exposed to the compound, and c) the amount of normalized translation from the XIAP IRES reporter cistron exposed to the compound, relative to the amount of normalized translation from the XIAP IRES reporter cistron not exposed to the compound is determined, wherein a relative increase in normalized translation from the XIAP IRES reporter cistron exposed to the compound indicates a compound that increases XIAP IRES-dependent protein translation, and wherein a relative decrease in translation from the XIAP IRES reporter cistron exposed to the compound indicates a compound that decreases XIAP IRES-dependent protein translation.

In other preferred embodiments of the fifth aspect of the invention, the XIAP IRES reporter cistron is exposed to a cell extract prior to being exposed to the test compound, or after being exposed to the test compound, and the cell extract is capable of translating the XIAP IRES reporter cistron.

In another preferred embodiment of the fifth aspect of the invention, the XIAP IRES reporter cistron is within a cell, and the cell is exposed to the test compound. The cell may further include a cistron that is not under the translational regulation of the XIAP IRES (i.e., an "internal control" cistron), and a) the amount of translation from the reporter cistron in the cell exposed to the compound is normalized relative to the amount of translation of the internal control cistron in the cell exposed to the compound, and b) the amount of translation from the reporter cistron in the cell not exposed to the compound is normalized relative to the amount of translation of the internal control cistron in the cell not exposed to the compound, and c) the amount of normalized translation from the reporter cistron in the cell exposed to the compound, relative to the amount of normalized translation from the reporter cistron in the cell not exposed to the compound is determined, wherein a relative increase in normalized translation from the reporter cistron in the cell exposed to the compound indicates a compound that increases XIAP IRES-dependent protein translation, and wherein a relative decrease in translation from the reporter cistron in the cell exposed to the compound indicates a compound that decreases XIAP IRES-dependent protein translation.

In a sixth aspect, the invention features a method for identifying a compound that modulates protein translation comprising: a) providing at least two reporter cistrons, wherein the reporter cistrons comprise a reporter cistron that is not under the translational regulation of a XIAP IRES (an "internal control" reporter cistron), and a reporter cistron that is under the translational regulation of a XIAP IRES (a "XIAP IRES" reporter cistron); b) exposing the reporter cistrons to the compound; c) determining the amount of translation from the internal control reporter cistron and the XIAP IRES reporter cistron; d) calculating the ratio of the amount of translation from the XIAP IRES reporter cistron to the amount of translation from the internal control reporter cistron (translation$_{cisXI/cisIC}$); and e) comparing translation$_{cisXI/cisIC}$ in a sample exposed to the compound to translation$_{cisXI/cisIC}$ in a sample not exposed to the compound. An increase in translation$_{cisXI/cisIC}$ indicates a compound that increases XIAP IRES-dependent translation and a decrease in translation$_{cisXI/cisIC}$ indicates a compound that decreases XIAP IRES-dependent translation.

In preferred embodiments of the sixth aspect of the invention, the reporter cistrons are exposed to a cell extract prior to being exposed to the test compound, or are exposed to a cell extract after being exposed to the test compound, and the cell extract is capable of translating the XIAP IRES reporter cistron.

In another preferred embodiment of the sixth aspect, the reporter cistrons are within a cell, and the cell is exposed to the test compound. In other embodiments of the sixth aspect the reporter cistrons may comprise a single transcription unit, and the internal control reporter cistron may be located upstream from the XIAP IRES reporter cistron.

In still other embodiments of the sixth aspect of the invention, the method may be used for identifying a compound that decreases (or increases) XIAP IRES-dependent translation, wherein translation$_{cisXI/cisIC}$ in a cell exposed to the compound is decreased (or increased) relative to translation$_{cisXI/cisIC}$ in a cell not exposed to the compound. A compound that decreases the XIAP IRES-dependent translation may be useful for treating cancer, and a compound that increases XIAP IRES-dependent translation may be useful for treating diseases or conditions that involve increased cell death, relative to normal conditions. Such disease or conditions may include, for example, myocardial infarction, neurodegenerative disease, organ loss or rejection, hair loss, or infertility.

In other embodiments of the sixth aspect of the invention, the method may further comprise a third reporter cistron (a "non-XIAP IRES" reporter cistron), wherein the non-XIAP IRES reporter cistron is under the translational regulation of an IRES that is not a XIAP IRES. In a preferred embodiment, the IRES that is not a XIAP IRES may be a VEGF IRES. In another preferred embodiment of the sixth aspect, the reporter cistrons may comprise a single transcription unit and the internal control reporter gene may be located upstream from the XIAP IRES reporter cistron and the non-XIAP IRES reporter cistron.

In yet another preferred embodiment of the sixth aspect, the method further comprises: f) calculating the ratio of the amount of translation from the non-XIAP IRES reporter cistron to the amount of translation from the internal control reporter cistron (translation$_{cisXI/cisIC}$; and g) comparing translation$_{cisXI/cisIC}$ in a sample exposed to the compound to translation$_{cisXI/cisIC}$ in a sample not exposed to the compound. An increase in translation$_{cisXI/cisIC}$ indicates a compound that increases non-XIAP IRES-dependent translation and a decrease in translation$_{cisXI/cisIC}$ indicates a compound that decreases non-XIAP IRES-dependent translation.

Moreover, in a further embodiment of the sixth aspect of the invention the method may be used for identifying a compound for treating cancer, wherein: a) translation$_{cisXI/cisIC}$ in a sample exposed to the compound is decreased relative to translation$_{cisXI/cisIC}$ in a cell not exposed to the compound, and b) translation$_{cisXI/cisIC}$ in a sample exposed to the compound is decreased relative to translation$_{cisXI/cisIC}$ in a sample not exposed to the compound, wherein the compound is useful for treating cancer.

In addition, in another embodiment of the sixth aspect of the invention, the method may be used for identifying a compound that inhibits apoptosis, wherein: a) translation$_{cisXI/cisIC}$ in a sample exposed to the compound is increased relative to translation$_{cisXI/cisIC}$ in a sample not exposed to the compound, and b) translation$_{cisXI/cisIC}$ in a sample exposed to the compound is increased relative to translation$_{cisXI/cisIC}$ in a sample not exposed to the compound, wherein the compound is useful for inhibiting apoptosis in a cell.

In a seventh aspect, the invention features a purified nucleic acid comprising a nucleotide sequence complementary to the nucleotide sequence of a XIAP IRES (XIAP IRES antisense nucleic acid). The XIAP IRES antisense nucleic acid may be complementary to nucleotide sequences of any of the XIAP IRES nucleic acids described in the first, second, or third aspects of the invention. The XIAP IRES antisense nucleic acid is at least 10 bases long, preferably, at least 18 bases long, more preferably, at least 25 bases long, even more preferably, at least 40, 60, 85, or 120 bases long, or even as long as a full-length IRES. The XIAP IRES antisense nucleic acid may be used as a probe for detecting a XIAP IRES nucleic acid, or may be used to inhibit the activity (e.g., regulation of translation) of a XIAP IRES.

In an eight aspect, the invention features a method for decreasing a cell's resistance to apoptosis, by introducing a purified XIAP IRES antisense nucleic acid into the cell, wherein the XIAP IRES antisense nucleic acid inhibits the translation of XIAP in the cell. In a preferred embodiment, the method is used to decrease a cancer cell's resistance to apoptosis. In another preferred embodiment, the cell is subjected to an apoptotic stimulus, such as a toxin or gamma irradiation after introduction of the XIAP antisense nucleic acid into the cell. In other preferred embodiments, the antisense nucleic acid comprises the sequence set forth in SEQ ID NOs: 6, 8, or 9.

In a ninth aspect, the invention features a method for stimulating apoptosis in a cell. The method includes introducing into the cell a purified nucleic acid encoding a polypeptide that stimulates apoptosis in the cell, wherein the coding region for the polypeptide is under the translational regulation of a XIAP IRES. In preferred embodiments of the ninth aspect of the invention, the cell is a cancer cell and the polypeptide is XIAP.

In a tenth aspect, the invention features a purified nucleic acid that hybridizes to a probe comprising at least ten consecutive nucleotides from the XIAP IRES sequence or a sequence complementary to a XIAP IRES, wherein the nucleic acid does not include the full XIAP-encoding cDNA sequence.

Still another aspect of the invention is a purified nucleic acid comprising a region that hybridizes to a probe comprising at least ten consecutive nucleotides from the XIAP IRES sequence or a sequence complementary to a XIAP IRES, said nucleic acid not being the full length murine or human XIAP gene or mRNA.

"Cap-dependent translation" means that a 7-methylguanosine cap must be present at the 5' end of an mRNA molecule in order to initiate translation of the mRNA into protein.

"Cap-independent translation" means that a 7-methylguanosine cap is not required for translation of an mRNA molecule. Cap-independent translation initiation mechanisms include ribosome re-initiation, ribosome shunting, and internal ribosome binding.

"IRES" means a region of a nucleic acid molecule, e.g., an mRNA molecule, that allows internal ribosome entry sufficient to initiate translation in an assay for cap-independent translation, such as the bicistronic reporter assay described herein. The presence of an IRES within an mRNA molecule allows cap-independent translation of a linked protein-encoding sequence that otherwise would not be translated.

"Sufficient to initiate translation" means that the presence of an IRES increases cap-independent translation by at least 10% (preferably by at least 20%, more preferably by at least 40%, and most preferably, by at least 60%), relative to cap-independent translation in the absence of an IRES.

"XIAP IRES" means a nucleic acid that has at least 60% (preferably at least 70%, more preferably at least 80%, even more preferably at least 90%, still more preferably at least 95%, yet more preferably at least 98%, and most preferably, 100%) sequence identity to a XIAP mRNA sequence, and, furthermore, is adjacent at its 5' or 3' end, to at least one nucleotide (a "variant" nucleotide) that is not present at that position in a naturally occurring XIAP gene or XIAP mRNA. A variant nucleotide must be positioned within 500 nucleotides of the 5' or 3' end of a XIAP IRES. XIAP IRES nucleotide sequences may be found upstream from mammalian (e.g., human or mouse) XIAP coding regions in naturally-occurring XIAP genes or mRNAs. Examples of XIAP IRES nucleotide sequences are the nucleotide sequences found within the region between approximately −265 and −1 relative to the human and mouse XIAP start codons. These human (SEQ ID NO: 2) and mouse (SEQ ID NO: 1) XIAP IRES sequences are shown in FIG. 4.

Other preferred XIAP IRES nucleotide sequences include: the sequence from −268 and −1 (human, SEQ ID NO: 19; mouse, SEQ ID NO: 20) relative to the human and mouse XIAP start codons; the sequence from −162 through −1 (human, SEQ ID NO: 21); the sequence from −161 through −1 (mouse, SEQ ID NO: 22); the sequence from −103 through −1 (human, SEQ ID NO: 23); the sequence from −102 through −1 (mouse, SEQ ID NO: 24); the sequence from −83 through −1 (human, SEQ ID NO: 25; mouse, SEQ ID NO: 26); the sequence from −162 through −35 (human, SEQ ID NO: 27); the sequence from −161 through −35 (mouse, SEQ ID NO: 28); the sequence from −268 through −35 (human, SEQ ID NO: 29); the sequence from −268 through −35 (mouse, SEQ ID NO: 30).

"Nucleic acid encoding a XIAP IRES" means nucleic acid that is template for transcription of a XIAP IRES.

"XIAP IRES antisense nucleic acid" means a nucleic acid complementary to a XIAP IRES nucleic acid sequence. Preferably, the antisense nucleic acid decreases cap-independent translation by at least 5%, more preferably by at least 10%, still more preferably by at least 20% or even 30%, and most preferably by at least 50%.

"Non-XIAP IRES" means an IRES that has less than 60% identity to the XIAP IRES, for example (but not limited to), a VEGF IRES, a c-myc IRES, an FGF-2 IRES, or a BiP IRES, all of which are known in the art.

"XIAP gene" means a genomic DNA or cDNA sequence that encodes XIAP.

"Cistron" means a "coding region," or segment of nucleic acid that encodes a single protein. Reporter cistron, as used within, means a segment of nucleic acid (an mRNA or a DNA molecule) that encodes a reporter gene product (see below). The reporter cistron may be under the translational control of an IRES, for example, the XIAP IRES or the VEGF IRES. A reporter cistron may be used as an internal control, according to which translation levels of other reporter genes or reporter cistrons are normalized. For example, FIG. 1B shows the results from an experiment in which translation of a CAT reporter cistron under the control of the XIAP IRES is normalized with respect to the β-gal reporter cistron that is not under the control of the XIAP IRES. An internal control reporter cistron, as used within, means a reporter cistron that is not under the control of a XIAP IRES.

"VEGF IRES" means an IRES encoded by the upstream region (i.e., upstream from the coding region) of a mammalian VEGF gene, which when present within an mRNA molecule, enhances translation of a downstream cistron in cells that are under conditions of hypoxia. The VEGF IRES is fully described in Stein, I., et al. *Mol. Cell. Biol.* 18:3112–9 (1998), hereby incorporated by reference.

"Transcription unit" means an mRNA molecule. A transcription unit contains at least one cistron (sequence that encodes a protein), and may contain two or more cistrons (i.e., the transcription unit may encode two or more proteins).

"Reporter gene" (herein used interchangeably with "reporter cistron") means any gene or translatable nucleotide sequence that encodes a product whose expression is detectable and/or quantitatable by immunological, chemical, biochemical or biological assays. A reporter gene product may, for example, have one of the following attributes, without restriction: fluorescence (e.g., green fluorescent protein), enzymatic activity (e.g., lacZ/β-galactosidase, luciferase, chloramphenicol acetyltransferase), toxicity (e.g., ricin), or an ability to be specifically bound by a second molecule (e.g., biotin or a detectably labelled antibody). It is understood that any engineered variants of reporter genes, which are readily available to one skilled in the art, are also included, without restriction, in the foregoing definition. A reporter gene or reporter cistron, as used herein, may be a DNA or mRNA molecule.

"XIAP IRES reporter cistron" means a reporter cistron that is under the translational regulation of a XIAP IRES.

"Internal control reporter cistron" means a reporter cistron that is not under the translational regulation of a XIAP IRES.

"Non-XIAP IRES reporter cistron" means a reporter cistron that is under the translational regulation of an IRES that is not a XIAP IRES.

"Translation$_{cisXI/cisIC}$" means the ratio of the amount of translation from a XIAP IRES reporter cistron to the amount of translation from an internal control reporter cistron.

"Translation$_{cisNX/cisIC}$" means the ratio of the amount of translation from a non-XIAP IRES reporter cistron to the amount of translation from an internal control reporter cistron.

"Reporter plasmid" means a DNA construct that carries a reporter gene or cistron under the transcriptional regulation of an operably linked promoter. Translation of the reporter gene or cistron may be under the control of a translational control element, for example, a XIAP IRES. If the reporter gene is linked to a translational control element, the level of reporter gene activity reflects translational control of the reporter gene or cistron.

"Bicistronic reporter plasmid" means a plasmid that contains two reporter genes or cistrons (e.g., β-gal and CAT) under the transcriptional control of a single promoter (e.g., the CMV promoter), such that transcriptional activation of the promoter results in the production of a single, bi-cistronic mRNA molecule encoding both the β-gal and CAT gene products.

"Modulating" means changing cap-independent translation, either by decrease or increase.

"A decrease" means a lowering in the level of translation, as measured by a decrease in reporter gene activity using a reporter gene assay, for example, lacZ/β-galactosidase, CAT, green fluorescent protein, luciferase, etc. The decrease is preferably at least 30%, more preferably 40%, and even more preferably 70%. For example, a decrease in cap-independent translation may be detected using ELISA to measure the level of protein translated from a given cistron. Analogous methods for measuring protein levels (or relative protein levels) also may be used.

"An increase" means a rise in the level of translation, as measured by an increase of reporter gene activity using a reporter gene assay, for example, lacZ/β-galactosidase, CAT, green fluorescent protein, luciferase, etc. Preferably, the increase is by at least 30%, more preferably by 40%, still more preferably by 70%, even more preferably by at least 2-fold, and most preferably by at least 3-fold. For example, an increase in cap-independent translation may be detected using ELISA to measure the level of protein translated from a given cistron. Analogous methods for measuring protein levels (or relative protein levels) also may be used.

"Promoter" means a minimal sequence sufficient to direct transcription. Also included in the invention are those promoter elements which are sufficient to render promoter-dependent gene expression controllable in a cell type-specific, tissue-specific, or temporal-specific manner, or inducible by external signals or agents; such elements may be located in the 5' or 3' or intron sequence regions of the native gene.

"Operably linked" means that a gene and one or more regulatory sequences are connected in such a way as to permit gene expression when the appropriate molecules (e.g., transcriptional activator proteins) are bound to the regulatory sequences.

"Expression vector" means a DNA construct that contains a promoter operably linked to a downstream gene, cistron, or RNA coding region (e.g., an antisense RNA coding region). Transfection of the expression vector into a recipient cell allows the cell to express RNA encoded by the expression vector. An expression vector may be a genetically engineered plasmid or virus, derived from, for example, a bacteriophage, adenovirus, retrovirus, poxvirus, herpesvirus, or artificial chromosome.

"Gene therapy vector" means an expression vector introduced into cells for the purpose of gene therapy.

"Expose" means to allow contact between an animal, cell, lysate or extract derived from a cell, or molecule derived from a cell, and a test compound.

"Test compound" means a chemical, be it naturally-occurring or artificially-derived, that is surveyed for its ability to modulate an alteration in reporter gene activity or protein levels, by employing one of the assay methods described herein. Test compounds may include, for example, peptides, polypeptides, synthesized organic molecules, naturally occurring organic molecules, nucleic acid molecules, and components thereof.

A "cell comprising a tissue" means a cell that is naturally a component of the tissue of interest, or a cell from an exogenous source that has been introduced into said tissue; for example, an angiogenic factor-secreting cell that is implanted into the heart for the purpose of increasing angiogenesis in the region of tissue into which the cell has been implanted.

"Substantially identical" means a nucleic acid exhibiting at least 50%, preferably 60%, more preferably 70%, still more preferably 80%, and most preferably 85% identity to a reference nucleic acid sequence. The length of sequences for comparison will generally be at least 50 nucleotides, preferably at least 60 nucleotides, more preferably at least 75 nucleotides, and most preferably at least 110 nucleotides.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

"Substantially pure DNA" means DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

"High stringency conditions" means conditions that allow hybridization comparable with that found using a DNA probe of at least 40 nucleotides in length, in a buffer containing 0.5 M NaHPO$_4$, pH 7.2, 7% SDS, 1 mM EDTA, and 1% BSA (fraction V), at a temperature of 65° C., or a buffer containing 48% formamide, 4.8× SSC, 0.2 M Tris-Cl, pH 7.6, 1× Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well-known by those skilled in the art of molecular biology. See, e.g., F. Ausubel et al., *Current Protocols in Molecular Biology*, John Wiley & Sons, New York, N.Y., 1994, hereby incorporated by reference.

"Transformation" or "transfection" means any method for introducing foreign molecules into a cell (e.g., a bacterial, yeast, fungal, algal, plant, insect, or animal cell, particularly a mammalian cell). Lipofection, DEAE-dextran-mediated transfection, microinjection, protoplast fusion, calcium phosphate precipitation, retroviral delivery, electroporation, and biolistic transformation are just a few of the methods known to those skilled in the art which may be used.

"Transformed cell" or "transfected cell" means a cell (or a descendent of a cell) into which a DNA molecule comprising an IRES and/or encoding a polypeptide of the invention has been introduced, by means of recombinant DNA techniques. Such cells may be either stably or transiently transfected.

"Protein" or "polypeptide" or "polypeptide fragment" means any chain of more than two amino acids, regardless of post-translational modification (e.g., glycosylation or phosphorylation), constituting all or part of a naturally-occurring polypeptide or peptide, or constituting a non-naturally occurring polypeptide or peptide.

"Apoptosis" means the process of cell death wherein a dying cell displays a set of well-characterized biochemical hallmarks which include cell membrane blebbing, cell soma shrinkage, chromatin condensation, and DNA laddering. Cells that die by apoptosis include neurons (e.g., during the course of neurodegenerative diseases such as stroke, Parkinson's disease, and Alzheimer's disease), cardiomyocytes (e.g., after myocardial infarction or over the course of congestive heart failure), and cancer cells (e.g., after exposure to radiation or chemotherapeutic agents). Environmental stress (e.g., hypoxic stress) that is not alleviated may cause a cell to enter the early phase of the apoptotic pathway, which is reversible (i.e., cells at the early stage of the apoptotic pathway can be rescued). At a later phase of apoptosis (the commitment phase), cells cannot be rescued, and, as a result, are committed to die.

Proteins and compounds known to stimulate and inhibit apoptosis in a diverse variety of cells are well-known in the art. For example, intracellular expression and activation of the caspase (ICE) family induces or stimulates apoptotic cell death, whereas expression of the Bcl-2 family inhibits apoptotic cell death. In addition, there are survival factors that inhibit cell death in specific cell types. For example, neurotrophic factors such as NGF inhibit neuronal apoptosis.

In some situations it may be desirable to artificially stimulate or inhibit apoptotic cell death by gene therapy or by a compound that mimics a gene therapeutic effect. For example, a cell that is susceptible to apoptosis induced by disease or environmental stress may be made more resistant to apoptosis by introducing an expression vector encoding an anti-apoptotic protein (such as a Bcl-2 family member or a neurotrophin) into the cell. Conversely, a cancer cell may be made less resistant to apoptosis by introducing into it an expression vector encoding a pro-apoptotic protein (such as a caspase). Placement of the encoded protein of interest under the translational regulation of a XIAP IRES ensures that copious quantities of the protein are produced, especially under cellular conditions during which most protein translation (i.e., cap-dependent protein translation) is down-regulated, e.g., when a cell is under environmental stress, and when a cell is at a threshold for entering the apoptotic pathway.

"Cell extract" means a preparation containing the contents of cells. The extract may be prepared simply by lysing cells (a cell lysate), or may involve additional purification steps, such as the elimination of membrane components or organelles, or enrichment of particular components of the cell lysate by methods known to those skilled in the art, such as centrifugation, differential precipitation, or chromatography. A cell extract, as used herein, is capable of cap-dependent and cap-independent (e.g., IRES-dependent) translation of a reporter cistron. Furthermore, a cell extract also may be capable of transcribing a reporter cistron prior to translation. Therefore, a reporter protein encoded by a reporter cistron may be translated by mixing either mRNA encoding the reporter cistron, or DNA having a promoter operably linked to the reporter cistron (e.g., an expression plasmid), with cell extract. Coupled transcription/translation systems are known in the art and are commercially available.

"Translation" as used herein and as used by those of skill in the art, refers the process of generating a polypeptide that has an amino acid sequence dictated by the codon sequence of an mRNA that encodes the polypeptide.

"Transcription" as used herein and as used by those of skill in the art, refers the process of using a DNA sequence as a template to generate a messenger RNA (mRNA) molecule of given nucleotide sequence.

BRIEF DESCRIPTION OF THE DRAWINGS

FIG. 1A is a diagram of bicistronic reporter gene constructs containing human or mouse XIAP 5' UTRs inserted upstream from the CAT gene.

FIG. 1B is a graph showing the relative CAT activity resulting from transfection of the constructs shown in FIG. 1A into HeLa cells.

DETAILED DESCRIPTION OF THE INVENTION

Figure 2:
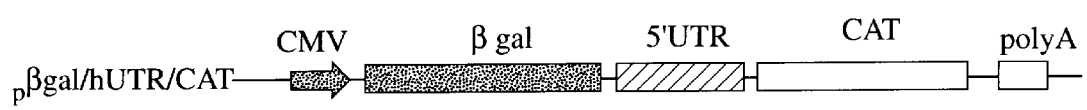
FIG. 2 is a diagram of a bicistronic reporter gene construct containing the human XIAP 1-kb 5' UTR inserted upstream from the CAT coding region.

We have discovered a novel genetic element for the regulation of protein expression, particularly under conditions of cell stress. The X-linked inhibitor of apoptosis protein (XIAP) plays a critical role in regulating cell death by inhibiting apoptosis. Several features of the XIAP mRNA suggested to us that XIAP may not be efficiently translated by a traditional, cap-dependent mechanism. These are: i) the presence of an unusually long 5' untranslated region (UTR) (>5.5 kb for murine, >1.6 kb for human XIAP transcripts), ii) the presence of numerous potential translation initiation sites upstream of the authentic initiation AUG codon, and iii) the high degree of secondary structure predicted for the 5'

UTR. Despite these characteristics, we have found the XIAP protein in abundance in all tissues examined, indicating that XIAP mRNA is efficiently translated.

Cap-dependent translation is partially or completely inhibited under certain conditions, such as during certain phases of the cell cycle, during growth arrest, following viral infection of a cell, and following the exposure of cells to environmental stress, such as hypoxic stress, induction of a heat shock response, or entry into the early, reversible phase of apoptosis. In contrast, cap-independent translation is not inhibited by factors that inhibit cap-dependent translation, and is often induced or enhanced under conditions that inhibit cap-dependent translation. We hypothesized that expression of XIAP via cap-independent translation enhances survival of a cell under stress. Accordingly, we tested whether the 5' UTR of XIAP mRNA regulates translation initiation in a manner independent of a cap-dependent, ribosome scanning mechanism.

Using bi-cistronic mRNA reporter constructs, we show that a 265 nt region from the 5' UTR of XIAP mRNA mediates initiation of translation by an internal ribosome entry site (IRES). Several lines of evidence indicate that the 5' UTR of XIAP functions via the IRES, as opposed to mediating ribosome readthrough and re-initiation between the two cistrons in bi-cistronic constructs.

First, the 5' UTRs of both human and mouse XIAP mRNA, which promote efficient translation of the second cistron in bicistronic constructs, are both large (1 kb and 1.4 kb respectively) and contain numerous initiation codons. We believe that efficient readthrough and re-initiation through such sequence would be unlikely.

Second, a truncated 5' UTR segment inserted upstream of the second cistron (in a bicistronic construct) in the reverse orientation fails to direct translation initiation of the second cistron. If enhanced readthrough and re-initiation (as opposed to specific binding of a ribosome to an IRES) were responsible for translation of the second cistron, then we should have observed increased reporter gene activity from reporter gene constructs containing a second cistron preceded by the reverse-oriented truncated (265 nt) 5' UTR, because readthrough and re-initiation would be more efficient with the short 265 nt 5' UTR segment than with the longer 1 kb and 1.4 kb 5' UTR segments.

The third and the most direct line of evidence for the existence of a XIAP IRES is our observation that translation of the second cistron in the bicistronic construct is resistant to the overexpression of the poliovirus protease 2A. The poliovirus protease 2A is known to cleave and inactivate the initiation factor eIF4G subunit of eIF4F, thereby inhibiting cap-dependent translation. Our results show that the 5' UTR of XIAP mRNA contains a functional IRES element.

Translation by cap-dependent scanning is known to be inhibited at specific stages of the cell cycle and by environmental insults that can lead to heat shock or growth arrest. Therefore, a cap-independent, IRES-directed, mechanism of translation is physiologically appropriate for synthesis of a protein that regulates apoptosis, since the presence of an IRES in the XIAP transcript allows for continuous production of the XIAP protein, thereby increasing protection against apoptosis following an initial insult. This selective production of XIAP is likely to be important for the biochemical decision-making process of survival versus apoptosis. As evidence of this, HeLa cells transfected with a construct expressing XIAP under the translational control of the XIAP 5' UTR displayed 30% higher survival following serum deprivation than did cells transfected with an expression construct containing the XIAP coding region alone.

Our data demonstrate that translation of a critical regulator of apoptosis, XIAP, is mediated by internal initiation. This mode of translation appears to be crucial for the appropriate expression of XIAP protein, and is correlated with increased survival following an initial apoptotic insult. The presence of an IRES element in the 5' UTR of XIAP, and possibly other mRNAs that encode anti-apoptotic proteins, may enhance cellular survival during exposure to transient apoptotic stimuli.

The finding that a XIAP IRES enhances cap-independent translation of a linked protein-encoding sequence suggests possible uses for the XIAP IRES in regulating protein translation. For example, XIAP IRES-encoding DNA may be used to increase the efficacy of gene therapy; this may be achieved by inserting the XIAP IRES-encoding DNA into a gene therapy vector, thereby enhancing cap-independent translation of a linked therapeutic protein. Moreover, intracellular delivery of XIAP IRES antisense nucleic acid to unwanted cells, such as cancer cells, may be used to inhibit translation of endogenous XIAP, thereby increasing cellular susceptibility to apoptosis. In addition, reporter gene constructs comprising a XIAP IRES linked to a reporter cistron may be used for the discovery of compounds that modulate cap-independent translation. Such compounds may be useful for stimulating or inhibiting apoptosis. Uses for the XIAP IRES are more fully described below.

Gene Therapy

The XIAP IRES sequence can be inserted into gene therapy vectors such that an encoded mRNA contains a protein-coding region under the translational control of the XIAP IRES. Proteins encoded by such XIAP IRES-containing vectors are more abundantly produced under cellular conditions that favor cap-independent translation, relative to proteins that are not under cap-independent translational control.

For example, cap-dependent translation is decreased in cells (such as cardiomyocytes) subjected to environmental stress (e.g. hypoxic stress in a failing heart); such cells are relatively more susceptible to apoptotic cell death. To render cardiomyocytes in a failing heart more resistant to hypoxia-induced cell death, a vector encoding a therapeutic protein such as an anti-apoptotic protein or an angiogenesis factor could be introduced into the cardiomyocytes. However, a vector encoding a therapeutic protein that is translated by a cap-dependent mechanism may not be fully effective, because the mRNA encoding the protein will not be efficiently translated in cells subjected to hypoxic stress, and the resulting protein levels would be low. A more effective gene therapy would take advantage of a mechanism that allows efficient translation of a therapeutic protein under environmental conditions that necessitate the presence of the therapeutic protein. Inclusion of a XIAP IRES sequence into the mRNA that encodes a therapeutic protein ensures that the protein is efficiently translated when required (e.g., under conditions of cellular stress).

Gene therapy vectors that encode therapeutic proteins under the translational regulation of a XIAP IRES are useful for expressing proteins in cells under conditions in which cap-independent translation is enhanced, as well as in cells under normal conditions. Cells in which cap-independent protein is enhanced include cells under environmental stress, cells undergoing a heat shock response, cells exposed to radiation, cells that are in the early, reversible phase of apoptosis, growth-arrested cells, and cells at the $G_0$–$G_1$ phase of the cell cycle. Therefore, vectors encoding therapeutic proteins under the translational control of a XIAP IRES may be useful for increasing survival in cells at risk for harmful apoptosis, such as in patients suffering from or at risk for autoimmune diseases or other degenerative diseases. Examples of cells and situations in which it would be desirable to inhibit apoptosis include, but are not limited to: neurons (e.g., in degenerative and autoimmune diseases of the central or peripheral nervous system, such as stroke, Alzheimer's disease, Parkinson's disease, multiple sclerosis, and amyotrophic lateral sclerosis) cardiomyocytes (e.g., in heart disease or post-myocardial infarction), skeletal myocytes (e.g., in muscular degenerative disease, such as Duchenne's muscular dystrophy), kidney and liver cells (e.g., in early stages of progressive organ failure from disease or exposure to toxins), hair follicle cells (e.g., in hair loss), ovarian follicle cells, ova, sperm cells (e.g., in infertility), pancreatic islet cells, e.g., beta cells (e.g., in autoimmune diabetes) or retinal photoreceptor cells (e.g., in retinal degenerative conditions such as those resulting from retinitis pigmentosa, chemical toxicity, retinal detachment, glaucoma, diabetes, and axotomy).

For example, retinitis pigmentosa is a heterogeneous collection of diseases characterized by progressive, irreversible loss of photoreceptors, which eventually leads to partial or complete blindness. Over 66 genes or genetic loci that can trigger retinal degeneration have been identified. Apoptosis has been demonstrated to occur in virtually all retinal pathologies, including retinitis pigmentosa, chemical toxicity, retinal detachment, glaucoma, diabetes, and axotomy. Suppression of apoptosis is expected to be of enormous clinical significance in treatment of retinal degenerative disease; moreover, the accessibility of the eye makes it relatively amenable to gene therapy. An appropriate expression vector (or mRNA) encoding an anti-apoptotic protein under the translational regulation of the XIAP IRES is administered to the eye such that it enters the photoreceptor cells and its encoded protein is expressed. The relatively high levels of anti-apoptotic protein resulting from XIAP IRES-regulated expression in cells under apoptotic stress decreases the susceptibility of the cells to apoptosis and thus slows disease progression. One example of such an anti-apoptotic protein is XIAP, which functions at the convergence of all apoptotic signaling pathways and therefore protects against a broad variety of cell death triggers.

Expression vectors encoding an anti-apoptotic protein (such as XIAP) or other therapeutic protein (e.g., a growth or angiogenesis factor) under the translational control of the XIAP IRES may also be introduced into cells ex vivo in order to enhance the survival of cell or organ transplants. For example, the vectors may be introduced into pancreatic beta cells prior to transplantion into diabetic patients or into dopaminergic neurons prior to transplantation into Parkinson's patients. Transplanted cells containing the expression vectors of the invention are more likely to survive in the patient after transplantation than cells not containing such vectors.

Vectors that encode polypeptides under the translational regulation of a XIAP IRES may also be useful for inducing growth-arrested cells to divide in a regulated manner; for example, enhancing translation, under hypoxic conditions, of a vector-encoded growth factor that induces cells to divide in culture, which would then provide sufficient cells for implantation into patients in need of such treatment.

In some situations it may be desirable to stimulate apoptosis, for example, in cancer cells or undesirable cells such as excess adipocytes. In such cases, gene therapy vectors that encode cell death-inducing proteins (e.g., caspase, p53, or bad) under the translational regulation of a XIAP IRES may be administered to enhance a cell's sensitivity to apoptosis.

Gene therapy vectors may employ tissue-specific promoters (e.g., a cardiomyocyte-, skeletal myocyte-, pancreatic beta cell-, or neuron-specific promoter, as a means of more precisely targeting expression of the therapeutic protein to the desired cell type.

Polypeptides that may be expressed under the translational regulation of the XIAP IRES include, but are not limited to, those shown in Table 1 below.

TABLE 1

| Protein | Genbank Accession Number |
| --- | --- |
| XIAP | U45880 |
| NAIP | U19251 |
| TIAP | SEQ ID NOS: 3 and 4 |
| HIAP1 | U45878 |
| HIAP2 | U45879 |
| VEGF | M63971 |
| BCL-2 | M13995 |
| BDNF | M61181 |
| NGF | X52599 |
| CNTF | X55890 |
| EPO | M11319 |
| Insulin | J00265 |
| TPO | S76771 |
| p53 | U94788 |
| VHL | AF010238 |
| XAF | X99699 |
| BAX | L22474 |
| $BCL-X_{L1}$ | Z23115 |
| BAD | AF031523 |
| $BCL-X_S$ | Z23116 |
| CASPASE-1 | U13698 |
| CASPASE-2 | U13021 |
| CASPASE-3 | U26943 |
| CASPASE-4 | Z48810 |
| CASPASE-5 | U28015 |
| CASPASE-6 | U20536 |
| CASPASE-7 | U37488 |
| CASPASE-8 | U58143 |
| CASPASE-9 | U60521 |
| CASPASE-10 | U60519 |
| b-FGF | M27968 (basic Fibroblast Growth Factor) |
| TRADD | L41690 |
| FADD | U24231 |
| NT-3 | M61180 |
| NT-4/5 | M86528 |
| GDNF | L19063 (Glial cell line Derived Neurotrophic Factor) |
| PDGF-B | X02811 (Platelet Derived Growth Factor B) |
| IGF2 | X03562 (Insulin-like Growth Factor II) |

Antisense Therapy

We have observed that apoptotic stimuli increase intracellular XIAP protein levels in a XIAP IRES-dependent manner, thereby providing increased resistance to apoptosis. However, in some cases (e.g., in cancer cells) it would be desirable to counteract this enhanced XIAP IRES-dependent apoptotic resistance. Inhibition of XIAP IRES-dependent translation using XIAP IRES-specific antisense therapy may be used to increase a cell's susceptibility to apoptosis.

Antisense therapy is based on the well-known principle of suppressing gene expression by intracellularly hybridization of endogenous nucleic acid (genomic DNA or mRNA) molecules encoding the protein of interest with a complementary antisense nucleic acid, such as an antisense oligonucleotide or antisense RNA; therefore, antisense nucleic acids inhibit protein expression at the transcriptional and/or at the translational level. Antisense oligonucleotides or antisense RNA, generated by well-known methods, may be administered to patients by conventional drug delivery techniques; the antisense nucleic acids enter the appropriate cell type and hybridize with the endogenous target nucleic acid to inhibit transcription or translation of the target protein. Antisense mRNA may also be provided intracellularly to a patient by administration of a gene therapy vector encoding an antisense RNA of interest. Expression of the antisense RNA may limited to a particular cell type, for example, by placing a cistron encoding the antisense RNA under the transcriptional regulation of a tissue-specific promoter.

XIAP IRES antisense nucleic acids contain at least 10 consecutive nucleotides that are complementary to a XIAP IRES mRNA or DNA sequence, and preferably contain at least 14–18 consecutive nucleotides that are complementary to a XIAP IRES mRNA or DNA. XIAP IRES antisense nucleic acids may contain at least 25, 40, 60, 85, 120, or more consecutive nucleotides that are complementary to a XIAP IRES mRNA or DNA, and may be as long as a full-length XIAP IRES.

Any region of the human XIAP IRES may be used as a target for antisense inhibition of XIAP translation, and particular sequences for XIAP IRES antisense nucleic acids may be selected by well-known approaches. For example, if desired, computer algorithms may be used to identify sequences that form the most stable hybridization duplexes. Computer algorithms may also be used to identify regions of the XIAP IRES that are relatively accessible within a folded mRNA molecule; antisense nucleic acids against such regions are more likely to effectively inhibit translation of XIAP mRNA. For example, the sequence at −153 through −139 of the human XIAP IRES DNA sequence (5'-GTTTCTTAGCGGTCG-3'; SEQ ID NO: 7; see FIG. 4) is predicted to be accessible for hybridization within endogenous XIAP mRNA; therefore, an antisense nucleic acid that is complementary this sequence, e.g., 5'-CGACCGCTAAGAAAC-3' (SEQ ID NO: 8) or 5'-CGACCGCUAAGAAAC-3' (SEQ ID NO: 9) is useful for decreasing endogenous XIAP levels, thereby increasing the sensitivity of a target cell to an apoptotic stimulus. Computer algorithms that may be used to identify optimal XIAP IRES sequences for generating antisense nucleic acids include, but are not limited to, OLIGO 5.0 from National Biosciences Inc. (http://www.sxst.it/nbi_olg.htm) and MFOLD (http://mfold2.wustl.edu/~mfold/rna/form1.cgi). References describing algorithms for predicting secondary structure are described in M. Zuker et al. "Algorithms and Thermodynamics for RNA Secondary Structure Prediction: A Practical Guide." in: *RNA Biochemistry and Biotechnology*, J. Barciszewski & B. F. C. Clark, eds., NATO ASI Series, Kluwer Academic Publishers (1999) and in Mathews et al. *J. Mol. Biol.* 288:911–940 (1999).

In addition, specific functional regions of the XIAP IRES may be targeted for antisense therapy. For example, we have found that the polypyrimidine tract at position −46 through −35 (5'-TGTTCTCTTTTT-3'; SEQ ID NO: 5; see FIG. 4) of the human XIAP IRES DNA sequence is necessary for XIAP IRES-dependent translation. Therefore, antisense nucleic acids, e.g., 5'-AAAAAGAGAACA-3' (SEQ ID NO: 6) targeting this region of the XIAP IRES may be used to inhibit XIAP IRES-dependent translation of endogenous XIAP.

Intracellular XIAP IRES antisense nucleic acid prevents transcription and/or translation of endogenous XIAP, thereby increasing a cell's susceptibility to apoptosis. Therefore, XIAP IRES antisense therapies are likely to prove useful in combination with traditional cancer therapy approaches, such as chemotherapy and radiation therapy, or in combination with other gene therapy approaches, e.g., expression of therapeutic anti-tumor proteins or other antisense tumor therapies.

Therapy

Nucleic acids of the invention and compounds identified using any of the methods disclosed herein may be administered to patients or experimental animals with a pharmaceutically-acceptable diluent, carrier, or excipient, in unit dosage form. Conventional pharmaceutical practice may be employed to provide suitable formulations or compositions to administer such compositions to patients or experimental animals. Although intravenous administration is preferred, any appropriate route of administration may be employed, for example, parenteral, subcutaneous, intramuscular, intracranial, intraorbital, ophthalmic, intraventricular, intracapsular, intraspinal, intracisternal, intraperitoneal, intranasal, aerosol, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found in, for example, "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for molecules of the invention include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Test Compounds

In general, novel drugs for modulation of XIAP IRES-dependent translation are identified from large libraries of both natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are generated, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their translation-modulatory activities should be employed whenever possible.

When a crude extract is found to modulate (i.e., increase or decrease) XIAP IRES-dependent translation, further fractionation of the positive lead extract is necessary to isolate chemical constituents responsible for the observed effect. Thus, the goal of the extraction, fractionation, and purification process is the careful characterization and identification of a chemical entity within the crude extract having an activity that stimulates or inhibits XIAP IRES-dependent translation. The same assays described herein for the detection of activities in mixtures of compounds can be used to purify the active component and to test derivatives thereof. Methods of fractionation and purification of such heterogenous extracts arc known in the art. If desired, compounds shown to be useful agents for treatment are chemically modified according to methods known in the art. Compounds identified as being of therapeutic value may be subsequently analyzed using mammalian models in which it is desirable to increase XIAP IRES-dependent translation (for example, to increase XIAP levels in cells that are susceptible to apoptosis, such as cardiomyocytes of an animal prone to myocardial infarctions), or decrease XIAP IRES-dependent translation (for example, to decrease XIAP levels in cancer cells, thus rendering them more susceptible to apoptosis induced by radiation or chemotherapeutic drugs).

Below are examples of high-throughput systems useful for evaluating the efficacy of a molecule or compound for increasing or decreasing XIAP IRES-dependent translation. Primary screens for compounds that modulate IRES-dependent, cap-independent translation.

The presence of a XIAP IRES within a transcription unit enables the cap-independent expression of a downstream reporter cistron. This finding allows us to provide assays for drugs that modulate XIAP IRES-dependent translation. For example, the amount of cap-independent translation of a reporter cistron under the translational regulation of a XIAP IRES may be determined from the amount of reporter protein (e.g., CAT, β-gal) activity encoded by the XIAP IRES-dependent reporter cistron. Relative translation of the XIAP IRES-dependent reporter cistron is measured in the presence and absence of a test compound, in comparison to a reference reporter cistron that is not under the translational control of a XIAP IRES. A reference reporter cistron may be (but is not necessarily) under the translational control of a non-XIAP IRES, such as a VEGF IRES, c-myc IRES, FGF-2 IRES, or another IRES known in the art.

Assays analogous to the one described above are readily adapted to high-throughput screens, such as those conducted in a 96-well microtiter plate or other high-throughput format, and reporter genes may be chosen specifically for their adaptability to a high-throughput format. For example, chemiluminescent assays for β-gal, CAT, and luciferase are commercially available and are easily used in high-throughput screening experiments, as reporter gene activity may be detected using a luminometer that accepts microtiter plates. Similarly, high-throughput reporter gene assays for GFP (green fluorescent protein) may be conducted using a fluorimeter with high-throughput capability.

Screens can be performed using virtually any cell type, or extracts derived therefrom, subject to the particular demands of each assay. For example, an assay involving whole cells requires that reporter gene cistrons (DNA or mRNA) may be readily introduced into the cells, e.g., by transfection or by microinjection. Selection of a particular type of cell to be used in a screening assay will also depend upon the ultimate goal of the assay. For example, cardiomyocyte extracts are useful for assays in which the goal is to identify compounds that modulate XIAP IRES activity in heart cells. And cells that undergo apoptosis in response to a given stimulus are useful for screening for a compound that stimulates IRES activity in cells on the verge of entering the apoptotic pathway. The best cell type for a particular screening assay will be apparent to one of skill in the art.

Compounds that are found to modulate XIAP IRES activity may be subjected to secondary screens as outlined below.

Secondary screens for compounds that modulate IRES-dependent, cap-independent translation.

After test compounds that appear modulate IRES-dependent translation are identified, it may be necessary or desirable to subject these compounds to further testing. The invention provides such secondary confirmatory assays.

For example, a compound that appears to modulate XIAP IRES-dependent translation can be tested for its effect on cap-independent translational regulation by other IRES elements, such as the VEGF, c-myc, or FGF-2 IRES elements. A compound may preferentially modulate XIAP IRES-dependent translation, or instead, may have additional effects on cap-independent protein translation in cells, by also modulating the activity of non-XIAP IRES elements. Such a compound may have the overall effect of inhibiting or stimulating apoptosis by modulating the translation levels of a group of proteins that are under the translational regulation of XIAP-like IRES elements.

A compound that enhances XIAP IRES-dependent translation can be tested to determine whether the compound inhibits apoptosis in various cells under various conditions. There are many in vitro and in vivo apoptosis induction models known in the art. Such assays can be used for testing the anti-apoptotic potential of a compound that enhances XIAP IRES-dependent translation. For example, cultured cells treated with a test compound can be tested for their relative resistance to apoptosis induced by hypoxia, growth factor withdrawal, or the addition of chemicals or cytokines (such as TNF). At later stages of testing, animals treated with a test compound can be tested for their resistance to tissue damage induced by myocardial infarction or stroke. A potential anti-apoptotic compound can be tested in animal models for other uses as well, such as for enhancing fertility or decreasing hair loss.

Likewise, a compound that decreases XIAP IRES-dependent translation may be useful in stimulating apoptosis of undesirable cells, such as cancer cells or excess adipocytes. A compound that is found to have apoptosis-stimulatory properties may be useful as a cancer treatment, either alone, or in conjunction with other cancer therapies.

Additional uses for compounds that modulate XIAP IRES-dependent translation will be apparent from the Gene Therapy section. A therapeutically useful compound is administered by one of the means described in the Therapy section.

The following examples are to illustrate the invention. They are not meant to limit the invention in any way.

EXAMPLE I

General Methods

Construction of bicistronic expression plasmids. The basic bicistronic vector pβgal/CAT was constructed by inserting the 0-galactosidase gene (NotI fragment) from plasmid pCMVβ (CLONTECH, Palo Alto, Calif.) and the chloramphenicol acetyltransferase gene (XbaI-BamHI fragment) from plasmid pCATbasic (Promega, Madison, Wis.) into the linker region of plasmid pcDNA3 (Invitrogen, Carlsbad, Calif.). The two cistrons are separated by a 100 bp intercistronic linker region containing a unique XhoI site. The expression of bi-cistronic mRNA is driven by a CMV promoter. The expression plasmid pCI-IRES/XIAP was constructed by inserting the 1 kb 5' UTR region of XIAP upstream of the XIAP coding region in the plasmid pCI (Invitrogen, Carlsbad, Calif.).

The XIAP 5' UTR elements of human and mouse XIAP were obtained by RT-PCR using human and mouse fetal liver Marathon-Ready cDNAs (CLONTECH, Palo Alto, Calif.) and XIAP primers containing an XhoI site. 5' UTR clones were inserted into the XhoI site of the intercistronic linker region of plasmid pβgal/CAT. The orientation and sequence of the 5' UTR fragments were confirmed by sequencing. The promoterless CAT reporter plasmid pCATbasic/UTR was constructed by inserting the −1007 to −1 human XIAP 5' UTR into the pCATbasic vector (Promega, Madison, Wis.) upstream of the CAT gene, as indicated in FIG. 1A.

Cell culture and transient DNA transfections. NIH 3T3 and HeLa cells were cultivated in Dulbecco modified Eagle medium (DMEM) supplemented with 10% fetal calf serum (FCS) and antibiotics. Transient DNA transfections were done using Lipofectamine (GIBCO BRL, Gaithersburg, Md.) according to the procedure recommended by the manufacturer. Briefly, cells were seeded at a density of $1 \times 10^5$ per 35 mm well and transfected 24 hours later in serum-free OPTI-MEM medium with 2 µg of DNA and 10 µl of Lipofectamine per well. The transfection mixture was replaced 4 hours later with DMEM supplemented with 10% FCS. For serum deprivation experiments, the cells were washed with PBS 24 hours post-transfection and then cultured in serum free DMEM. Cells extracts were prepared 24 hours post-transfection and β-gal and CAT activities were measured.

β-gal and CAT analysis. Transiently transfected cells were harvested in PBS 24 hr post-transfection and cell extracts were prepared by the freeze-thaw method as described (MacGregor, G. R., ct al., "Gene Transfer and Expression Protocols," pp. 217–235. In: *Methods in Molecular Biology*, Vol. 7, E. J. Murray and J. M. Walker (eds.), Humana Press Inc., Clifton, N.J., 1991). β-gal enzymatic activity in cell extracts was determined by spectrophotometric assay using ONPG (MacGregor et al., supra). CAT activity was determined by liquid scintillation method as described (Seed, B. and Sheen, J. Y., *Gene*, 67:271–7, 1998).

Cell death assays. HeLa cells were seeded at a density of $6 \times 10^4$ cells per 1 cm well and transfected 24 hours later as described above. Cells were washed with serum-free DMEM 24 hours post-transfection and were subsequently grown in serum-free DMEM. Cell viability was assessed at various time intervals using a calorimetric assay that measures cleavage of the tetrazolium salt WST-1 (Boehringer Mannheim, Indianapolis, Ind.) by mitochondrial dehydrogenases in viable cells. Assays were performed according to the procedure recommended by the supplier. The fraction of surviving cells was calculated from three separate experiments performed in triplicate.

RNA isolation and Northern blot analysis. Total RNA was prepared by guanidine isothiocyanate/phenol-chloroform extraction method using the TRIZOL reagent (GIBCO BRL, Gaithersburg, Md.) according to the procedure recommended by the supplier. RNA was denatured in formamide and separated on a 0.8% agarose gel. RNA was then transferred onto a Biodyne nylon membrane (GIBCO BRL, Gaithersburg, Md.) and was hybridized with CAT or lacZ DNA probes labeled with $^{32}P$ using a Rediprime random primer labeling kit (Amersham, Malvern, Pa.). Membranes were exposed to X-ray film (Kodak, Rochester, N.Y.) overnight using an intensifying screen (Amersham Malvern, Pa.).

EXAMPLE II

The 5' UTR of XIAP mRNA mediates translation of the second open reading frame in bi-cistronic mRNAs.

The 5' UTRs of both human and murine XIAP mRNAs are unusually long (>1.6 kb and >5.5 kb respectively). Both contain a polypyrimidine tract about 30 nucleotides (nt) upstream of the initiation AUG codon and contain numerous upstream AUG codons. To test whether regions in the 5' UTR could initiate translation by an internal ribosome entry mechanism, we constructed bi-cistronic mRNA transcripts (FIG. 1A) similar to those reported elsewhere (Pelletier, J., et al., *Nature*, 334:320–5, 1988). The vector pβgal/CAT directs transcription of bi-cistronic mRNA in which the first cistron, encoding β galactosidase (β-gal), is translated by a conventional cap-dependent mechanism. The second cistron encoding chloramphenicol acetyltransferase (CAT), however, can be translated only if the preceding linker region contains an internal ribosome entry site (IRES).

Plasmid constructs containing 1 kb of human or 1.4 kb of mouse XIAP 5' UTR sequence (FIG. 1A) were transfected into HeLa and NIH 3T3 cell lines, and the expression of both CAT and β-gal reporter genes was monitored. Briefly, DNA segments corresponding to indicated regions of the 5' UTR of human (h) or mouse (mn) XIAP transcript were inserted into the XhoI site of the linker region (LR) of the bi-cistronic plasmid pβgal/CAT. HeLa cells were transfected with the plasmids shown in FIG. 1A using Lipofectamine, and after 24 hours, cell extracts were prepared and β-galactosidase and CAT activities were determined (FIG. 1B). All constructs produced comparable amounts of β-gal activity, which was then used as in internal control to normalize for transfection efficiency of different plasmids. The translation of the second cistron was then determined by measuring CAT activity. The bars represent the average ±SD of five independent transfections.

Constructs containing the 5' UTR of either human or mouse XIAP mRNA directed translation of CAT reporter mRNA in both cell lines at 150-fold higher levels than constructs lacking the 5' UTR, or having the 5' UTR in the reverse orientation (FIG. 1B). Identical results were obtained from transfection of NIH 3T3 cells.

To eliminate the possibility that CAT translation was enhanced because the 5' UTR regions contained cryptic promoters, both 5' UTRs were cloned into the promoter-less CAT reporter plasmid pCATbasic (Promega, Madison, Wis.) and CAT activity was assayed; no CAT activity was detected in either case. We conclude that RNA sequences in the 5' UTR of the human and murine XIAP genes are capable of directing cap-independent translation of a downstream mRNA.

EXAMPLE III

Translation directed by the XIAP 5' UTR element is not inhibited by poliovirus protease 2A.

Following poliovirus infection, a rapid inhibition of host-cell protein synthesis is observed. This inhibition is mediated largely by the expression of viral protease 2A, which cleaves the eIF4G subunit of the cap-binding initiation factor eIF4F complex. Although cap-dependent cellular protein synthesis is inhibited, viral proteins are efficiently synthesized by an IRES-directed, cap-independent translation initiation. We tested whether expression of the 2A protease would affect translation initiation directed by the XIAP 5' UTR by co-expressing a bi-cistronic expression plasmid containing 1 kb of human XIAP 5' UTR (FIG. 2) with an expression plasmid encoding 2A protease in HeLa cells. HeLa cells were co-transfected with plasmids pβgal/hUTR/CAT (2 μg) and pCMV-2A (2 μg) or the control plasmid pcDNA3 (2 μg) using 10 Al of Lipofectamine, and β-galactosidase and CAT activities were determined 48 hours post-transfection. Expression of each reporter cistron assayed in control transfections was set at 100%.

Figure 3:
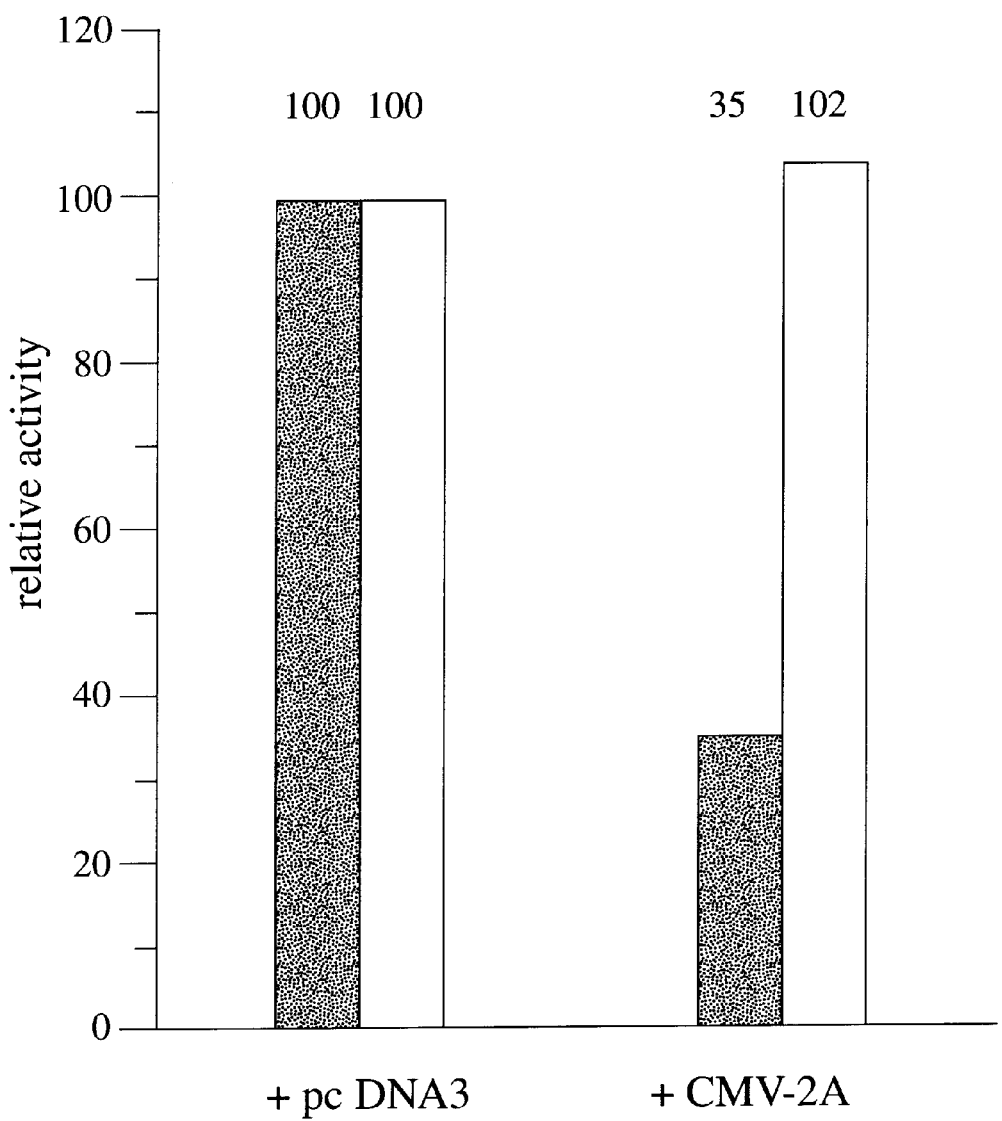
FIG. 3 is a graph showing β-gal and CAT activity after transfection of the construct shown in FIG. 2, plus and minus a protease 2A expression plasmid.

In the presence of 2A protease, translation of the first cistron, β-galactosidase, was reduced to 33% of control levels, whereas translation of the second, XIAP 5' UTR-directed CAT cistron remained unchanged (FIG. 3). These results indicate that the XIAP 5' UTR mediates true cap-independent translation, which is independent of the presence of intact eIF4G. This result confirms the hypothesis that the 5' UTR contains an internal ribosome binding site (IRES), as opposed to mediating translation by splicing or ribosome reinitiation, both of which are inhibited by protease 2A expression.

EXAMPLE IV
The XIAP IRES element is within a 265 nt fragment of conserved 5' UTR.

Figure 4:
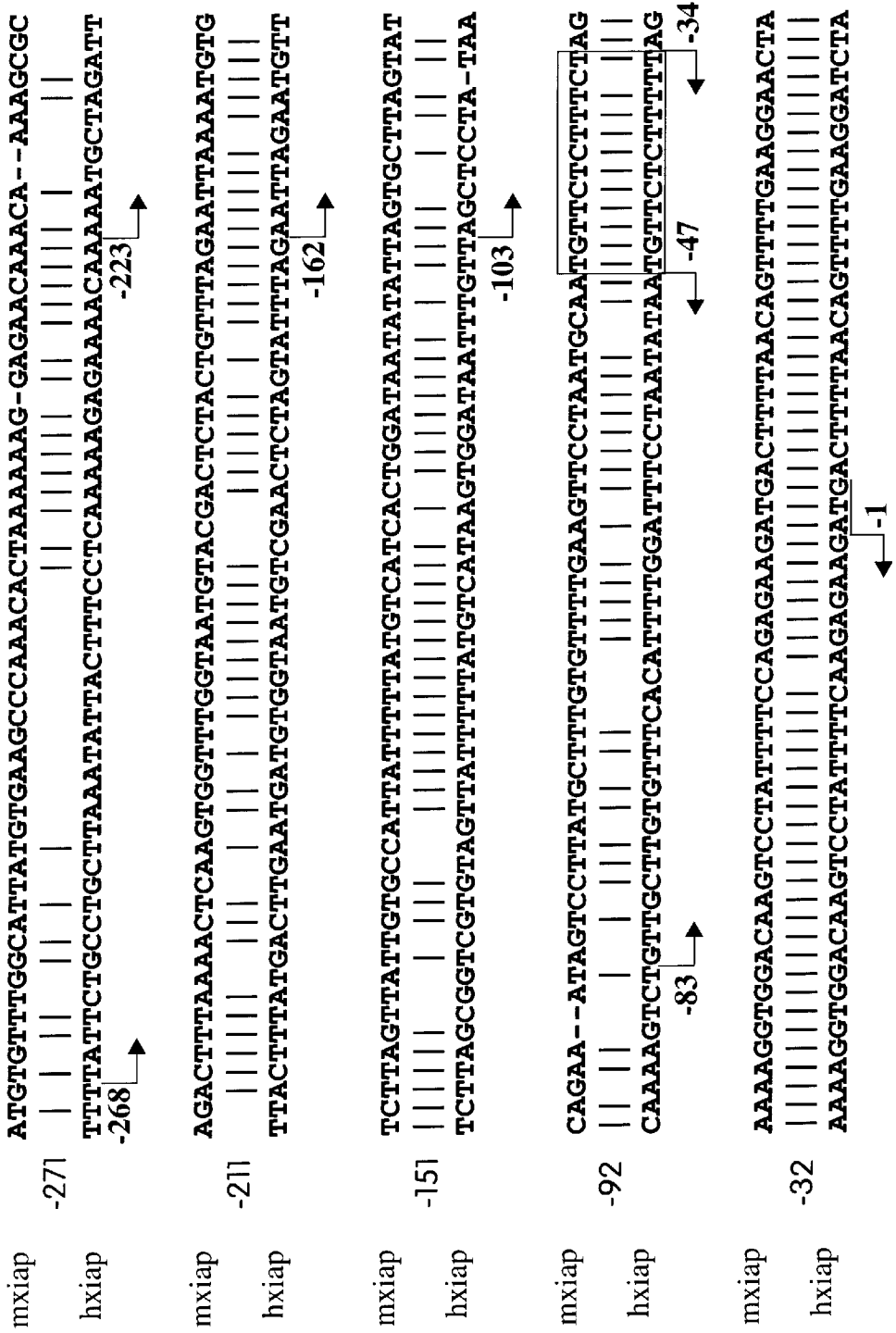
FIG. 4 is a diagram of a nucleotide sequence alignment of the mouse (SEQ ID NO: 1) and human (SEQ ID NO: 2) XIAP IRES elements and XIAP translation start sites.

We noted that although the homology of human and mouse XIAP genes within the coding region is 87%, the homology outside the coding region is confined to the region extending 270 nt upstream of the initiation codon. FIG. 4 shows a sequence comparison of the 5' UTR of mouse and human XIAP immediately upstream of the initiation AUG codon (underlined; position +1). The critical polypyrimidine tract is boxed, and deletions made to define the boundaries of the IRES element are indicated by arrows. Numbering is relative to the initiation codon (AUG).

Figures 5A, 5B:
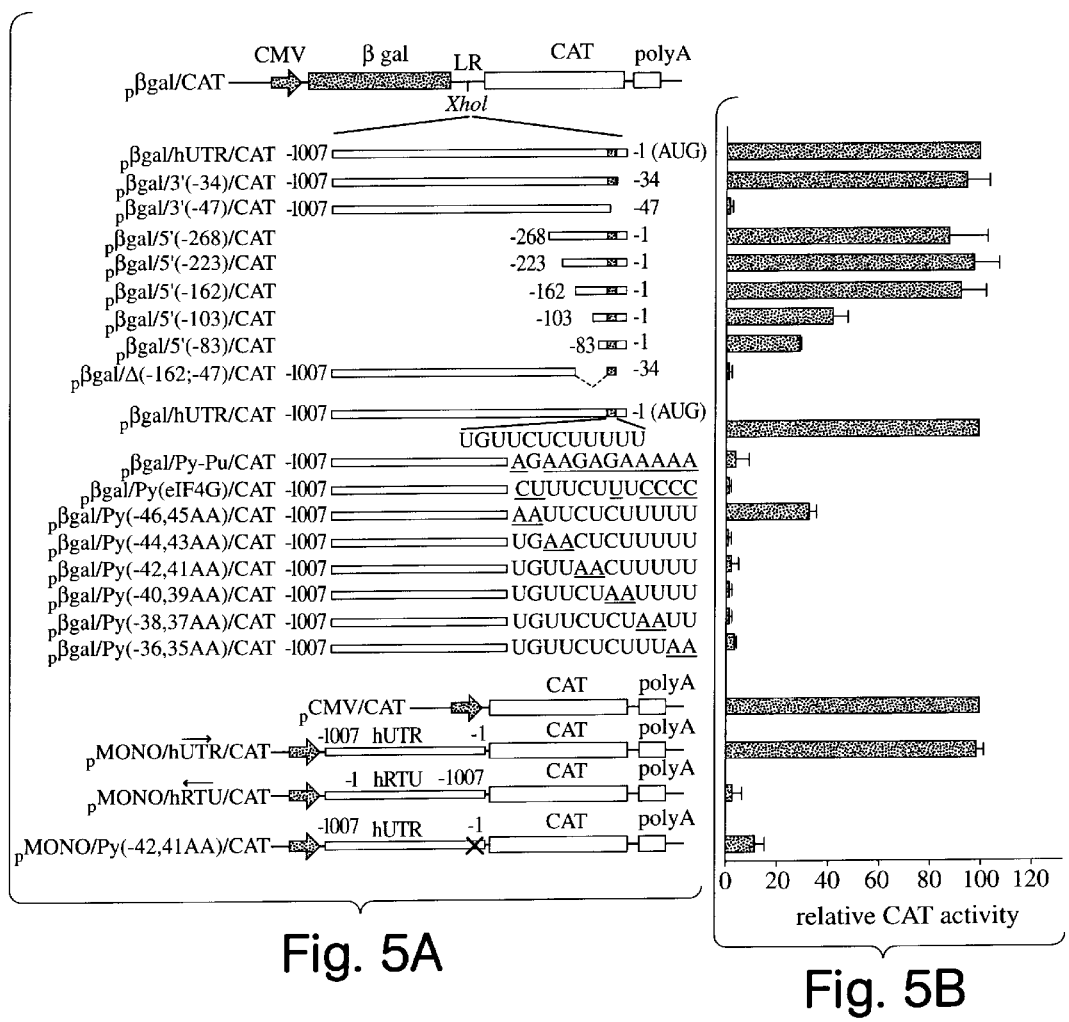
FIG. 5A is a diagram showing bicistronic and monocistronic reporter gene constructs used for deletion and mutation analyses of the human XIAP 5' UTR.
FIG. 5B is a graph showing the relative CAT activity resulting from transfection of the deletion constructs shown in FIG. 5A.

To determine the portion of the XIAP 5' UTR responsible for translation initiation, we generated constructs containing defined deletions of the human XIAP 5' UTR. DNA segments corresponding to indicated regions of the XIAP 5' UTR were cloned into the linker region (LR) of the bi-cistronic reporter plasmid pβ-gal/CAT (FIG. 5A; black box indicates the polypyrimidine tract) and tested their ability to initiate translation of the second cistron, represented by relative CAT activity (FIG. 5B). Plasmids with mutated PPT were constructed by PCR-directed mutagenesis. The RNA sequence of the PPT in each construct is indicated in FIG. 5A and base substitutions are underlined (SEQ ID NOs: 10–18). Monocistronic plasmids were constructed by deleting the βgal cistron (cloned into the Not I restriction site) from respective plasmids.

Briefly, HeLa cells were Lipofectamine-transfected with the plasmids shown in FIG. 5A. After 24 hours, cell extracts were prepared and β-galactosidase and CAT activities were determined. Relative CAT activity was calculated by normalizing with β-gal activity. The bars represent the average ±SD of three independent transfections.

To determine which part of the 5' UTR of XIAP mRNA is responsible for translation initiation, constructs containing defined deletions of the human XIAP 5' UTR were generated (FIG. 5A). The region that retained full IRES activity was the −162 to −1 nt segment upstream of the initiation codon which was as effective as the larger 5' UTR. The smallest construct that we made contained only 83 nt of the 5' UTR. While this construct had only 25% activity of the full length XIAP UTR, this activity was still 30-fold higher than the bi-cistronic mRNA containing no IRES. In monocistronic plasmids, the presence of a 5' UTR in the sense orientation did not reduce translation of the reporter gene, whereas in the antisense orientation, or with the mutation in the IRES (see below) translation was substantially reduced, implying that the translation of XIAP is fully dependent on the IRES (FIG. 5B, bottom).

There is a polypyrimidine tract (PPT) located 34 nt (i.e., from nt −35 through nt −46; see FIG. 4) upstream of the XIAP initiation codon. With the exception of the IRES element of eIF4G, this sequence is not present in any cellular IRES described so far. Therefore, we wished to determine if the PPT is important for XIAP IRES function. While the sequence between the initiation codon and the PPT is dispensable for XIAP IRES function, deletion of the PPT abolished IRES activity completely (FIG. 5B). Specifically, pβgal/3'(−34)/CAT, which contains −1007 through −35 of the human XIAP IRES, maintains full IRES activity (FIGS. 5A and 5B), as does a construct containing −268 through −35 of the human XIAP IRES. A construct containing −162 through −35 of the human XIAP IRES shows significant, but less that 100%, IRES activity.

We next deleted the −162 to −47 nt segment from the 5' UTR to test whether the PPT itself is sufficient for directing translation in bi-cistronic constructs. The −162 to −47 nt deletion, however, completely abolished IRES activity demonstrating that while the PPT sequence is necessary, it is not sufficient for internal ribosome entry. To determine sequence specificity of the PPT we constructed several base substitution mutants (FIG. 5B). The substitution of pyrimidines for purines drastically reduced IRES activity indicating the need for the PPT. When the PPT of XIAP IRES was replaced with the PPT of eIF4G IRES element, IRES activity was reduced to less than 2%. Base substitutions in every position in the PPT completely abolished IRES activity, except in positions −46 and −45 which retained some activity (38% of wild type sequence). These results suggest that a specific sequence within the PPT is critical for XIAP IRES activity. This specificity is in marked contrast to the IRES of eIF4G, the only other cellular IRES with polypyrimidine tract, where the wild-type sequence of the PPT is not critical.

EXAMPLE V
The XIAP IRES element mediates translation during serum starvation.

Figure 6:
FIG. 6 is a diagram of a bicistronic reporter gene construct containing the human XIAP 265-nucleotide 5' UTR upstream from the CAT coding region (pβgal/hIRES 265/CAT).

Translation of capped mRNAs is known to be inhibited following growth arrest, heat shock or during mitosis. In some cases, growth arrest induced by serum deprivation is followed by induction of apoptosis. We have shown previously that XIAP is a potent inhibitor of apoptosis induced by variety of signals including serum deprivation (Liston, et al., Nature, 379:349–353, 1996). We tested whether the XIAP IRES element could direct translation during the onset of apoptosis triggered by serum deprivation. A bi-cistronic reporter construct (pβgal/hIRES 265/CAT; FIG. 6) containing a 265 nt human IRES element upstream from the CAT (downstream) cistron was Lipofectamine-transfected into HeLa cells. After 24 hr of serum deprivation the relative levels of translation of both cistrons was measured by reporter gene assay. Expression of each reporter cistron assayed in control transfections was set at 100%. The experiment was carried out three times, with <10% variation between transfections.

Figure 7:
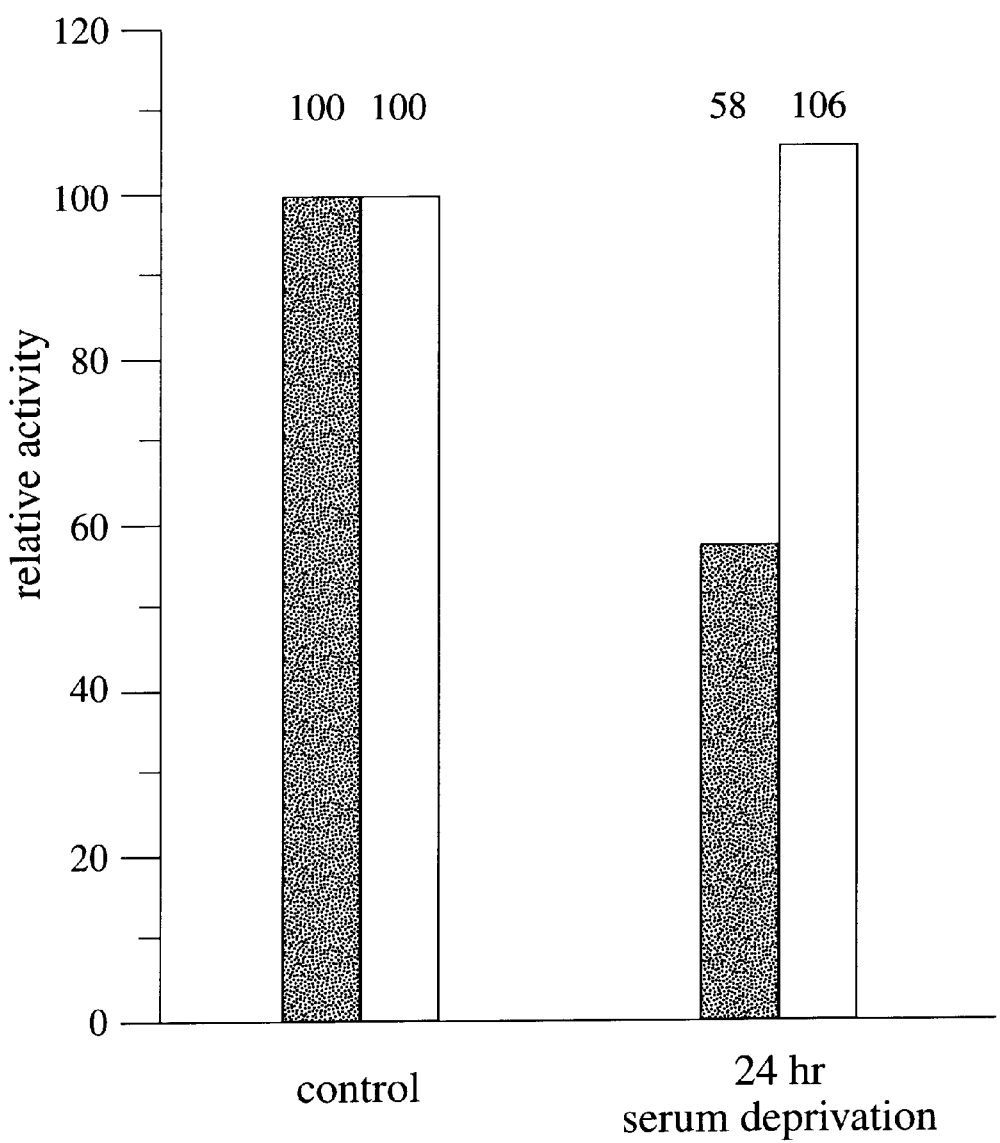
FIG. 7 is a graph showing β-gal and CAT activities in cells that were serum-starved after transfection.

Translation of the first cistron was reduced to 58% of control (non-starved cells), whereas translation of the second, IRES-directed cistron remained unchanged (FIG. 7). This indicates that the XIAP IRES element enhances translation in cells under environmental stress, such as serum deprivation.

EXAMPLE VI

XIAP-mediated inhibition of apoptosis is enhanced by the XIAP IRES element.

We and others have demonstrated that the overexpression of XIAP protects cells against apoptosis triggered by various stimuli (Liston, P., et al., *Nature*, 379:349–53, 1996; Uren, A. G., et al., *Proc. Natl. Accad. Sci. USA*, 93:4974–8, 1996). In these experiments, however, only the coding region of the XIAP transcript was used. If the translation of XIAP is mediated by the IRES element located within its 5' UTR, then overexpression of a transcript containing the XIAP IRES should offer increased protection following an apoptotic trigger relative to the protection conferred by the XIAP coding region alone.

To test this hypothesis, we transfected HeLa cells with either an expression plasmid containing the XIAP coding region plus 1 kb of 5' UTR, or a similar construct lacking the 5' UTR region, and tested the ability of both constructs to suppress apoptosis triggered by serum starvation. HeLa cells were Lipofectamine-transfected with expression plasmid pCI-lacZ, pCI-XIAP or pCI-IRES/XIAP. After 24 hours, the cells were washed with PBS and cultured in fresh serum-free medium. Cell viability at various time intervals was assessed by calorimetric assay using the WST-1 reagent (Boehringer Mannheim). The fraction of surviving cells was calculated from three separate experiment performed in triplicate.

Figure 8:
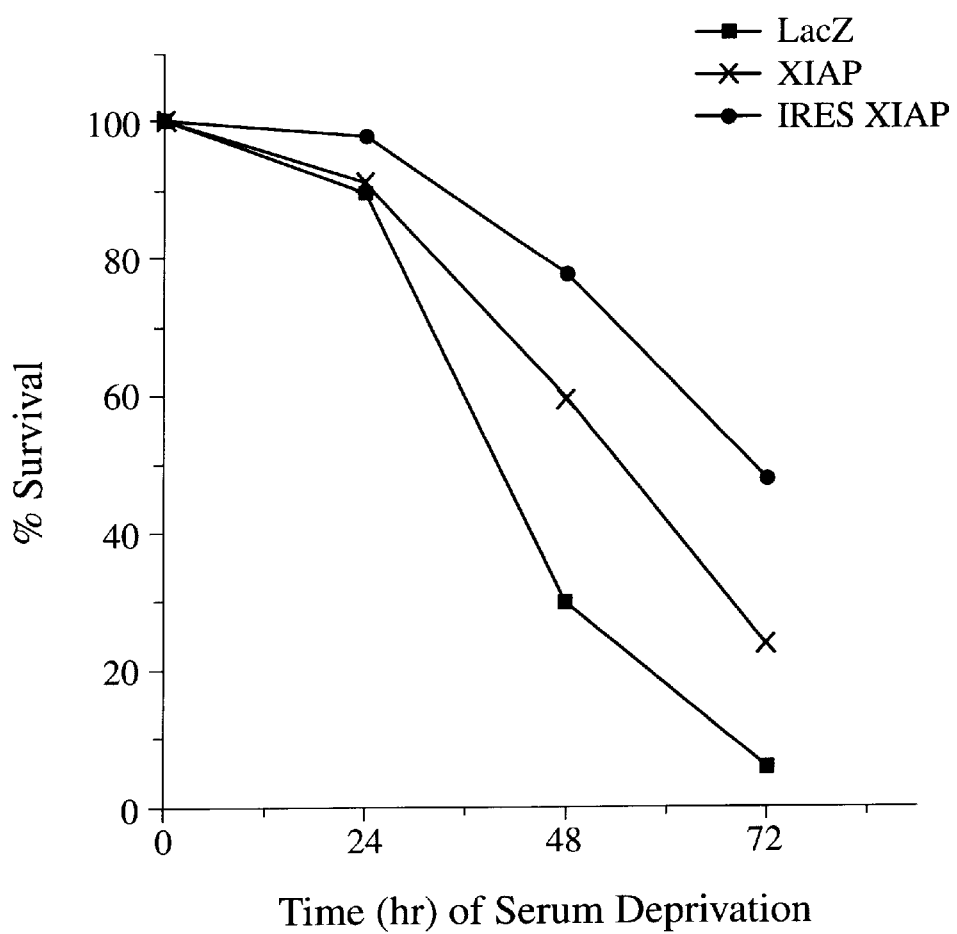
FIG. 8 is a graph showing the survival of serum-deprived cells transfected with an expression plasmid encoding either XIAP alone or XIAP under the translational regulation of the XIAP IRES.

At all time points following transfection, IRES-XIAP protected cells from apoptosis more efficiently than did the XIAP coding region alone (FIG. 8). These results clearly demonstrate that translation of XIAP is mediated by internal ribosome entry and that this mechanism is critical for XIAP function in vivo.

EXAMPLE VII

The XIAP IRES element mediates translation in cells exposed to ionizing radiation and apoptotic stress.

Figure 9:
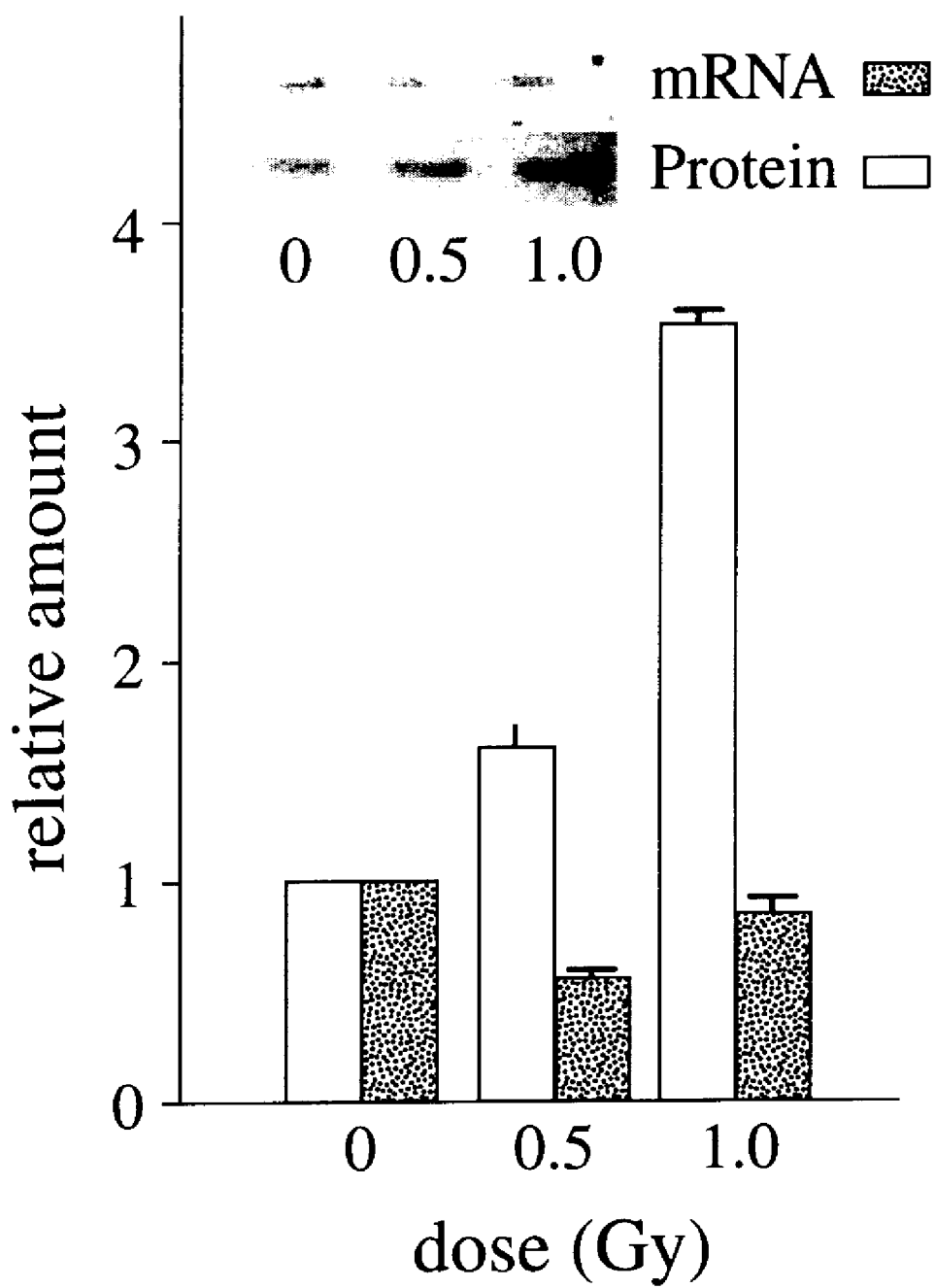
FIG. 9 is a graph showing that exposure to radiation up-regulates the XIAP protein level in H661 non-small cell lung carcinoma cells.

Our research has focused upon the physiological relevance of IRES-mediated XIAP translation under different paradigms of cellular stress. First, to determine whether endogenous XIAP IRES-directed translation is affected by cellular stress, we exposed cells of the non-small cell lung carcinoma cell line H661 to low-dose gamma irradiation and analyzed the resulting XIAP mRNA and protein levels by Northern and Western blot analysis. Changes in XIAP levels were analyzed densitometrically and normalized for levels of GAPDH (mRNA) or total protein loaded (average ±SD of three experiments; FIG. 9 inset shows representative blots). We observed that the low dose irradiation resulted in a 3.5 fold up-regulation of XIAP protein in the non-small cell lung carcinoma cell line H661, whereas the level of XIAP mRNA remained unchanged (FIG. 9). The expression pattern of other IAP genes (HIAP 1, HIAP2, and NAIP) did not change.

We hypothesized that the increase in XIAP protein observed after low-dose irradiation resulted from up-regulation of XIAP IRES-dependent translation. To test this hypothesis, we transfected H661 cells with the bi-cistronic XIAP IRES construct pβgal5'(268)/CAT (5 µg) using the SuperFect Transfection Reagent (30 µl; QIAGEN, Los Angeles, Calif.), incubated the cells for 12 hours after the transfection procedure, irradiated the cell with $^{60}$Co gamma rays at dose rate of approximately 1.5 Gy/min, and measured the relative translation of both cistrons at 12 hours post-irradiation. While the expression of the cap-dependent β-galactosidase was reduced to 51% of non-irradiated cells, the expression of the IRES-driven CAT reporter was increased (FIG. 10, right), supporting the hypothesis that the up-regulation of endogenous XIAP protein observed in irradiated cells is mediated by the IRES sequence.

Figure 10:
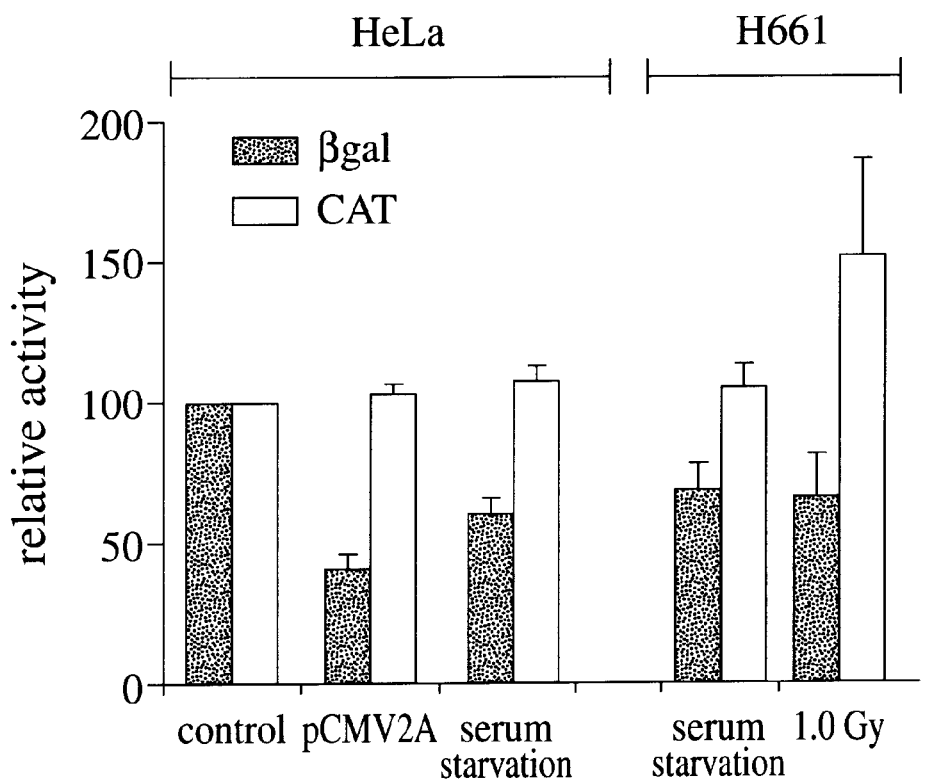
FIG. 10 is a graph showing that the XIAP IRES-dependent translation is resistant to cellular stresses that inhibit cap-dependent translation, such as expression of poliovirus protease 2A, serum starvation, and exposure to radiation.

Other cellular stresses such as poliovirus infection, growth arrest, hypoxia or heat shock are also known to inhibit cap-dependent, but not IRES-dependent, translation. We asked whether the XIAP IRES element is resistant to protein synthesis shut-off triggered by an overexpression of poliovirus protease 2A or serum withdrawal (FIG. 10, left). For the protease 2A overexpression experiment, HeLa cells were co-transfected with plasmids pβgal/5'(−268)/CAT (2 µg) and pCMV-2A (2 µg) or the control plasmid pcDNA3 (2 µg) as described in Example I, and β-galactosidase and CAT activities were determined 48 hours post-transfection. For the serum deprivation experiment, HeLa cells were transfected with the pβgal/5'(−268)/CAT (2 µg), the transfected cells were deprived of serum for 24 hours, and the β-galactosidase and CAT activities were determined. Expression of each reporter cistron assayed in the control transfection (FIG. 10, far left) was set at 100%. In both cases the translation of the cap-dependent reporter was reduced, whereas the translation of the XIAP IRES-driven reporter remained unchanged (FIG. 10, left; bars represent the average ±SD of three independent transfections).

Figure 11:
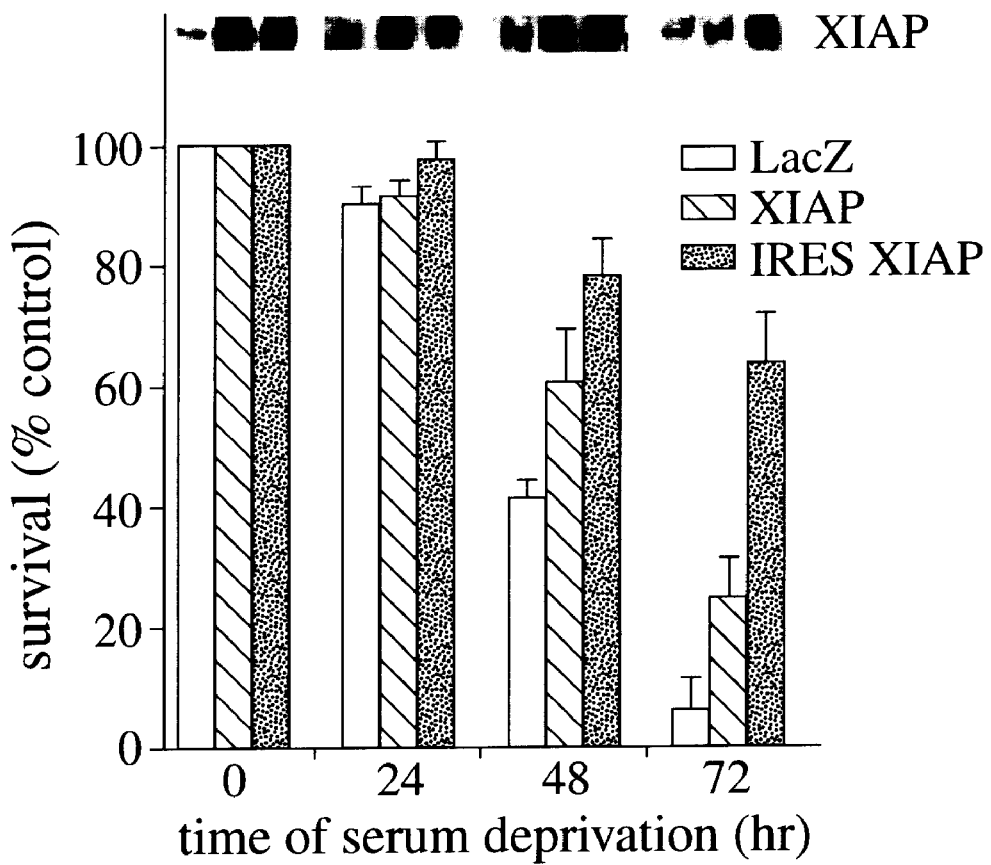
FIG. 11 is a graph showing that XIAP mRNA containing a XIAP IRES is more efficiently translated and results in higher resistance to serum-induced apoptosis than does XIAP mRNA lacking the XIAP IRES.

Overexpression of XIAP has been clearly shown to protect cells against apoptosis triggered by various stimuli including serum withdrawal. In these experiments, however, only the coding region of the xiap transcript was used. We then reasoned that if the translation of XIAP is mediated by the IRES element located within its 5' UTR, the overexpression of a XIAP transcript containing the XIAP IRES should offer greater protection following an apoptotic trigger than that seen with a transcript containing the XIAP coding region alone. To test this hypothesis, HeLa cells were transfected with either pCI-XIAP, pCI-IRES/XIAP, or pCI-lacZ (negative control) as described in Example I. After 24 hours, the cells were washed with PBS and grown in fresh serum-free medium. The viability of the cells at 0, 24, 48, and 72 hours of serum deprivation was assessed by a calorimetric assay that measures cleavage of the tetrazolium salt WST-1. At all time points following transfection and serum starvation of HeLa cells, the IRES-XIAP construct protected cells from apoptosis more efficiently than did the XIAP coding region alone (FIG. 11; bars represent the fraction of surviving cells ±SD of three independent experiments performed in triplicate). The inset at the top of FIG. 11 shows a representative Western blot demonstrating the relative XIAP protein levels in cells transfected with the various constructs (10 µg of total protein were loaded per lane). By 72 hours of serum starvation it was clear that the amount of XIAP protein produced from the IRES-XIAP construct exceeded that produced from the construct containing the XIAP coding region alone, although the levels of xiap mRNA transcribed from both plasmids were the same.

In order to initiate studies addressing the biological significance of the internal initiation of XIAP, we tested several cell lines for their ability to translationally up-regulate XIAP in response to cellular stress. Our results show that IRES-mediated translational up-regulation of endogenous XIAP without concomitant upregulation of XIAP mRNA varies in response to different triggers of cellular stress in different cell lines (Table 2). While serum deprivation upregulated XIAP protein in all cell lines tested (HeLa, HEL, 293, SHY5Y), low dose irradiation induced XIAP translation only in one (H661), possibly two (H520) cell lines. Notably the H661 cell line is most resistant of the four cell lines to radiation-induced apoptosis. A general response of the cell to apoptotic stress is the shut-off of cap-dependent protein synthesis. The presence of IRES would, therefore, allow for the continuous production of XIAP, even under conditions of stress. The degree of responsiveness of the IRES element would dictate the cellular threshold to apoptotic stimuli. This threshold level would be set according to the intrinsic properties of the cell or could be manipulated by the external stimulation of IRES-mediated XIAP translation. In either case, the induction of XIAP protein would be of potential benefit in the survival of the cell under acute but transient apoptotic conditions.

TABLE 2

Relative levels of XIAP protein and mRNA in response to cellular stress.

| Cell line | Stress trigger | Relative levels of XIAP* | |
|---|---|---|---|
| | | Protein | mRNA |
| H661 (non-small cell carcinoma, lung) | 1.0 Gy | 3.33 ± 0.05 | 0.85 ± 0.07 |
| H460 (non-small cell carcinoma, lung) | 1.0 Gy | 0.34 ± 0.14 | 0.76 ± 0.11 |
| H520 (squamous carcinoma, lung) | 1.0 Gy | 1.41 ± 0.25 | 0.76 ± 0.06 |
| SKOV3 (adenocarcinoma, ovary) | 1.0 Gy | 0.73 ± 0.07 | 0.83 ± 0.19 |
| HeLa (cervical carcinoma) | 72 hr SW | 2.03 ± 0.10 | 0.91 ± 0.07 |
| 293 (human embryonic kidney) | 72 hr SW | 2.17 ± 0.32 | 0.80 ± 0.16 |

TABLE 2-continued

Relative levels of XIAP protein and mRNA in response to cellular stress.

| Cell line | Stress trigger | Relative levels of XIAP* | |
|---|---|---|---|
| | | Protein | mRNA |
| HEL (human embryonic lung) | 72 hr SW | 1.95 ± 0.04 | 0.83 ± 0.09 |
| SHY5Y (neuroblastoma) | 72 hr SW | 1.75 ± 0.32 | 0.78 ± 0.16 |

*endogenous levels of XIAP protein (Western blot) and mRNA (Northern blot or Ribonuclease Protection Assay) were analyzed following either 1.0 Gy ionizing irradiation, or serum withdrawal (SW) for 72 hours. Changes in XIAP levels were analyzed densitometrically, normalized for levels of GAPDH (mRNA) or total protein loaded and compared to untreated controls which were set as 1 (average ± SD).

Other Embodiments

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth, and follows in the scope of the appended claims.

What is claimed is:

1. A method for identifying a compound that modulates protein translation, said method comprising:
   a) providing a x-linked inhibitor of apoptosis internal ribosomal entry site (XIAP IRES) reporter cistron, wherein said XIAP IRES has greater than 60% identity to one of SEQ ID NOS: 1, 2, or 19–30;
   b) exposing said XIAP IRES reporter cistron to a test compound,
   c) determining the amount of translation from said XIAP IRES reporter cistron exposed to said compound, relative to the amount of translation from said XIAP IRES reporter cistron not exposed to said compound, wherein a relative increase in translation from said XIAP IRES reporter cistron exposed to said compound indicates a compound that increases XIAP IRES-dependent protein translation, and wherein a relative decrease in translation from said XIAP IRES reporter cistron exposed to said compound indicates that a compound that decreases XIAP IRES-dependent protein translation.

2. The method of claim 1, wherein said XIAP IRES reporter cistron is exposed to a cell extract prior to being exposed to said test compound, said cell extract being capable of translating said XIAP IRES reporter cistron.

3. The method of claim 1, wherein said XIAP IRES reporter cistron is exposed to a cell extract after being exposed to said test compound, said cell extract being capable of translating said XIAP IRES reporter cistron.

4. The method of claim 1, further comprising providing an internal control reporter cistron, wherein:
   a) the amount of translation from said XIAP IRES reporter cistron exposed to said compound is normalized relative to the amount of translation of said internal control reporter cistron exposed to said compound, and
   b) the amount of translation from said XIAP IRES reporter cistron not exposed to said compound is normalized relative to the amount of translation of said internal control reporter cistron not exposed to said compound, and
   c) the amount of normalized translation from said XIAP IRES reporter cistron exposed to said compound, relative to the amount of normalized translation from said XIAP IRES reporter cistron not exposed to said compound is determined, wherein a relative increase in normalized translation from said XIAP IRES reporter cistron exposed to said compound indicates a compound that increases XIAP IRES-dependent protein translation, and wherein a relative decrease in translation from said XIAP IRES reporter cistron exposed to said compound indicates a compound that decreases XIAP IRES-dependent protein translation.

5. The method of claim 1, wherein said XIAP IRES reporter cistron is within a cell, and wherein said cell is exposed to said test compound.

6. The method of claim 5, wherein said cell further comprises an internal control reporter cistron, and wherein:

a) the amount of translation from said reporter cistron in said cell exposed to said compound is normalized relative to the amount of translation of said internal control cistron in said cell exposed to said compound, and b) the amount of translation from said reporter cistron in said cell not exposed to said compound is normalized relative to the amount of translation of said internal control cistron in said cell not exposed to said compound, and c) the amount of normalized translation from said reporter cistron in said cell exposed to said compound, relative to the amount of normalized translation from said reporter cistron in said cell not exposed to said compound is determined, wherein a relative increase in normalized translation from said reporter cistron in said cell exposed to said compound indicates a compound that increases XIAP IRES-dependent protein translation, and wherein a relative decrease in translation from said reporter cistron in said cell exposed to said compound indicates a compound that decreases XIAP IRES-dependent protein translation.

7. A method for identifying a compound that modulates protein translation, said method comprising;

a) providing at least two reporter cistrons, wherein said reporter cistrons comprise an internal control reporter cistron and a XIAP IRES reporter cistron, wherein said XIAP IRES has greater than 60% identity to one of SEQ ID NOS: 1, 2, or 19–30;

b) exposing said XIAP IRES reporter cistron to a test compound;

c) determining the amount of translation from said internal control reporter cistron (IC) and said XIAP IRES reporter cistron (XI);

d) calculating the translation$_{cisXI/cisIC}$;

e) comparing the translation$_{cisXI/cisIC}$ in a sample exposed to said compound to translation$_{cisXI/cisIC}$ in a sample not exposed to said compound, wherein an increase in translation$_{cisXI/cisIC}$ indicates a compound that increases XIAP-IRES-dependent translation and wherein a decrease in translation$_{cisXI/cisIC}$ indicates a compound that decrease XIAP IRES-dependent translation.

8. The method of claim 7, wherein said reporter cistrons are exposed to a cell extract prior to being exposed to said test compound, said cell extract being capable of translating said XIAP IRES reporter cistron.

9. The method of claim 7, wherein said reporter cistrons are exposed to a cell extract after being exposed to said test compound, said cell extract being capable of translating said XIAP IRES reporter cistron.

10. The method of claim 7, wherein said reporter cistrons are within a cell, and wherein said cell is exposed to said test compound.

11. The method of claim 7, wherein said reporter cistrons comprise a single transcription unit.

12. The method of claim 7, wherein said internal control reporter cistron is located upstream from said XIAP IRES reporter cistron.

13. The method of claim 7, wherein said method is for identifying a compound that decreases XIAP IRES-dependent translation, wherein translation$_{cisXI/cisIC}$ in a cell exposed to said compound is decreased relative to translation$_{cisXI/cisIC}$ in a cell not exposed to said compound.

14. The method of claim 13, wherein said method is for identifying a compound useful for treating cancer.

15. The method of claim 7, wherein said method is for identifying a compound that increases XIAP IRES-dependent translation, wherein translation$_{cisXI/cisIC}$ in a cell exposed to said compound is increased relative to translation$_{cisXI/cisIC}$ in a cell not exposed to said compound.

16. The method of claim 7, further comprising a non-XIAP IRES reporter cistron, wherein said non-XIAP IRES reporter cistron is under the translational regulation of an IRES that is not a XIAP IRES.

17. The method of claim 16, wherein said IRES that is not a XIAP IRES is a VEGF IRES.

18. The method of claim 16, wherein said reporter cistrons comprise a single transcription unit and wherein said internal control reporter gene is located upstream from said XIAP IRES reporter cistron and said non-XIAP IRES reporter cistron.

19. The method of claim 16, wherein said method further comprises:

f) calculating the translation$_{cisNX/cisIC}$;

g) comparing translation$_{cisNX/cisIC}$ in a sample exposed to said compound to translation$_{cisNX/cisIC}$ in a sample not exposed to said compound, wherein an increase in translation$_{cisNX/cisIC}$ indicates a compound that increases non-XIAP IRES-dependent translation and wherein a decrease in translation$_{cisNX/cisIC}$ indicates a compound that decreases non-XIAP IRES-dependent translation.

20. The method of claim 19, wherein said method is for identifying a compound for treating cancer, wherein:

a) translation$_{cisXI/cisIC}$ in a sample exposed to said compound is decreased relative to translation$_{cisXI/cisIC}$ in a cell not exposed to said compound, and b) translation$_{cisXI/cisIC}$ in a sample exposed to said compound is decreased relative to translation$_{cisNX/cisIC}$ in a sample not exposed to said compound, wherein said compound is useful for treating cancer.

21. The method of claim 19, wherein said method is for identifying a compound that inhibits apoptosis, wherein:

a) translation$_{cisXI/cisIC}$ in a sample exposed to said compound is increased relative to translation$_{cisXI/cisIC}$ in a sample not exposed to said compound, and b) translation$_{cisNX/cisIC}$ (in a sample exposed to said compound is increased relative to translation$_{cisNX/cisIC}$ in a sample not exposed to said compound, wherein said compound is useful for inhibiting apoptosis in a cell in need thereof.

22. A method for regulating protein translation in a cell, said method comprising introducing into said cell a purified nucleic acid encoding a polypeptide, wherein the coding region for said polypeptide is under the translational regulation of a XIAP IRES, wherein said XIAP IRES has greater than 60% identity to one of SEQ ID NOS: 1, 2, or 19–30, and wherein the presence of said XIAP IRES increases the level of cap-independent translation of said polypeptide, and further wherein said introducing is in vitro.

23. The method of claim 22, wherein said polypeptide is selected from the group consisting of NAIP, TIAP, HIAP1, HIAP2, VEGF, BCL-2, BDNF GDNF, PDGF-B, IGF-2, NGF CTNF, NT-3, NT-4/5, EPO, insulin, TPO, p53, VHL, XAF, BAX, BCL-X$_{L1}$, TRADD, FADD, BAD, BCL-X$_{S}$, and caspases 1, 2, 3, 4, 5 6, 7, 8, 9, and 10.

24. A method for decreasing a cell's resistance to apoptosis, said method comprising introducing into said cell in vitro, an antisense nucleic acid having a sequence complementary to at least 10 consecutive nucleotides of a XIAP IRES, wherein said XIAP IRES has greater than 60% identity to one of SEQ ID NOS: 1, 2, or 19–30, and wherein said antisense nucleic acid inhibits translation of XIAP in said cell in vitro.

25. The method of claim 24, wherein said cell is exposed to an apoptotic stimulus, wherein said apoptotic stimulus is gamma irradiation or a toxin.

26. The method of claim 22 or 24, wherein said cell is a cancer cell.

27. The method of claim 22, wherein said cell is at risk for undergoing apoptosis due to an autoimmune disease, a degenerative disease, or an immunorejection reaction.

28. The method of claim 22, wherein said polypeptide is a polypeptide that stimulates apoptosis.

29. The method of claim 22, wherein said polypeptide is a polypeptide that inhibits apoptosis, and wherein if said polypeptide is XIAP, said nucleic acid comprises at least one variant nucleotide within a 500 nucleotide region 5' or 3' to said XIAP IRES, said variant nucleotide being a nucleotide that is not present at the position of said variant nucleotide in a naturally occurring XIAP mRNA, relative to the position of said XIAP IRES.

* * * * *

SEQUENCE LISTING

<160> NUMBER OF SEQ ID NOS: 30

<210> SEQ ID NO 1
<211> LENGTH: 295
<212> TYPE: DNA
<213> ORGANISM: Mus musculus

<400> SEQUENCE: 1

```
atgtgtttgg cattatgtga agcccaaaca ctaaaaaagg agaacaaaca aaagcgcaga      60
ctttaaaact caagtggttt ggtaatgtac gactctactg tttagaatta aaatgtgtct     120
tagttattgt gccattattt ttatgtcatc actggataat atattagtgc ttagtatcag     180
aaatagtcct tatgctttgt gttttgaagt tcctaatgca atgttctctt tctagaaaag     240
gtggacaagt cctattttcc agagaagatg acttttaaca gttttgaagg aacta          295
```

<210> SEQ ID NO 2
<211> LENGTH: 299
<212> TYPE: DNA
<213> ORGANISM: Homo sapiens

<400> SEQUENCE: 2

```
ttttattctg cctgcttaaa tattactttc ctcaaaaaga gaaaacaaaa atgctagatt      60
ttactttatg acttgaatga tgtggtaatg tcgaactcta gtatttagaa ttagaatgtt     120
tcttagcggt cgtgtagtta tttttatgtc ataagtggat aatttgttag ctcctataac     180
```

```
aaaagtctgt tgcttgtgtt tcacattttg gatttcctaa tataatgttc tcttttttaga      240 aaaggtggac aagtcctatt ttcaagagaa gatgactttt aacagttttg aaggatcta       299
```

<210> SEQ ID NO 3
<211> LENGTH: 711
<212> TYPE: DNA
<213> ORGANISM: Homo sapiens

<400> SEQUENCE: 3

```
atgacgggtt atgaagcccg gctcattact tttgggacat ggatgtactc cgtcaacaaa       60
gagcagcttg caagagctgg attttatgct ataggtcaag aggataaagt acagtgcttt      120
cactgtggag gagggctagc caactggaag cccaaggaag atccttggga acagcatgct      180
aaatggtatc caggttgcaa atatctgcta gaagagaagg gacatgaata tataaacaac      240
attcatttaa cccgttcact tgagggagct ctggtacaaa ctaccaagaa acaccatca       300 ctaactaaaa gaatcagtga taccatcttc cctaatccta tgctacaaga agctatacga      360
atgggatttg atttcaagga cgttaagaaa ataatggagg aaagaattca acatctggg       420 agcaactata aaacgcttga ggttcttgtt gcagatctag tgagcgctca gaaagacact      480
acagaaaatg aattgaatca gacttcattg cagagagaaa tcagccctga gagccgcta      540 aggcgtctgc aagaggagaa gctttgtaaa atctgcatgg acagatatat cgctgttgtt      600
tttattcctt gtggacatct ggtcacttgt aaacaatgtg ctgaagcagt tgacagatgt      660
cccatgtgca gcgcggttat tgatttcaag caaagagttt ttatgtctta a               711
```

<210> SEQ ID NO 4
<211> LENGTH: 236
<212> TYPE: PRT
<213> ORGANISM: Homo sapiens

<400> SEQUENCE: 4

```
Met Thr Gly Tyr Glu Ala Arg Leu Ile Thr Phe Gly Thr Trp Met Tyr
  1               5                  10                  15

Ser Val Asn Lys Glu Gln Leu Ala Arg Ala Gly Phe Tyr Ala Ile Gly
                 20                  25                  30

Gln Glu Asp Lys Val Gln Cys Phe His Cys Gly Gly Gly Leu Ala Asn
             35                  40                  45

Trp Lys Pro Lys Glu Asp Pro Trp Gln His Ala Lys Trp Tyr Pro
     50                  55                  60

Gly Cys Lys Tyr Leu Leu Glu Glu Lys Gly His Glu Tyr Ile Asn Asn
 65                  70                  75                  80

Ile His Leu Thr Arg Ser Leu Glu Gly Ala Leu Val Gln Thr Thr Lys
                 85                  90                  95

Lys Thr Pro Ser Leu Thr Lys Arg Ile Ser Asp Thr Ile Phe Pro Asn
            100                 105                 110

Pro Met Leu Gln Glu Ala Ile Arg Met Gly Phe Asp Phe Lys Asp Val
        115                 120                 125

Lys Lys Ile Met Glu Glu Arg Ile Gln Thr Ser Gly Ser Asn Tyr Lys
    130                 135                 140

Thr Leu Glu Val Leu Val Ala Asp Leu Val Ser Ala Gln Lys Asp Thr
145                 150                 155                 160

Thr Glu Asn Glu Leu Asn Gln Thr Ser Leu Gln Arg Glu Ile Ser Pro
                165                 170                 175

Glu Glu Pro Leu Arg Arg Leu Gln Glu Glu Lys Leu Cys Lys Ile Cys
```

-continued

```
                180             185             190
Met Asp Arg Tyr Ile Ala Val Val Phe Ile Pro Cys Gly His Leu Val
                    195             200             205

Thr Cys Lys Gln Cys Ala Glu Ala Val Asp Arg Cys Pro Met Cys Ser
        210             215             220

Ala Val Ile Asp Phe Lys Gln Arg Val Phe Met Ser
225             230             235

<210> SEQ ID NO 5
<211> LENGTH: 12
<212> TYPE: DNA
<213> ORGANISM: Homo sapiens

<400> SEQUENCE: 5
tgttctcttt tt                                                          12

<210> SEQ ID NO 6
<211> LENGTH: 12
<212> TYPE: DNA
<213> ORGANISM: Homo sapiens

<400> SEQUENCE: 6
aaaaagagaa ca                                                          12

<210> SEQ ID NO 7
<211> LENGTH: 15
<212> TYPE: DNA
<213> ORGANISM: Homo sapiens

<400> SEQUENCE: 7
gtttcttagc ggtcg                                                       15

<210> SEQ ID NO 8
<211> LENGTH: 15
<212> TYPE: DNA
<213> ORGANISM: Homo sapiens

<400> SEQUENCE: 8
cgaccgctaa gaaac                                                       15

<210> SEQ ID NO 9
<211> LENGTH: 15
<212> TYPE: RNA
<213> ORGANISM: Homo sapiens

<400> SEQUENCE: 9
cgaccgcuaa gaaac                                                       15

<210> SEQ ID NO 10
<211> LENGTH: 12
<212> TYPE: RNA
<213> ORGANISM: Homo sapiens
<220> FEATURE:
<221> NAME/KEY: variation
<222> LOCATION: (1)...(1)
<223> OTHER INFORMATION: Wild-type polypyrimidine tract.

<400> SEQUENCE: 10
uguucucuuu uu                                                          12

<210> SEQ ID NO 11
<211> LENGTH: 12
<212> TYPE: RNA
```

```
<213> ORGANISM: Homo sapiens
<220> FEATURE:
<221> NAME/KEY: variation
<222> LOCATION: (1)...(12)
<223> OTHER INFORMATION: Positions 1 and 3-12 are mutated.

<400> SEQUENCE: 11
agaagagaaa aa                                                              12

<210> SEQ ID NO 12
<211> LENGTH: 12
<212> TYPE: RNA
<213> ORGANISM: Homo sapiens
<220> FEATURE:
<221> NAME/KEY: variation
<222> LOCATION: (1)...(12)
<223> OTHER INFORMATION: Positions 1-2, 7, and 8-12 are mutated.

<400> SEQUENCE: 12 cuucuuucc cc                                                               12

<210> SEQ ID NO 13
<211> LENGTH: 12
<212> TYPE: RNA
<213> ORGANISM: Homo sapiens
<220> FEATURE:
<221> NAME/KEY: variation
<222> LOCATION: (1)...(2)
<223> OTHER INFORMATION: Positions 1-2 are mutated.

<400> SEQUENCE: 13
aauucucuuu uu                                                              12

<210> SEQ ID NO 14
<211> LENGTH: 12
<212> TYPE: RNA
<213> ORGANISM: Homo sapiens
<220> FEATURE:
<221> NAME/KEY: variation
<222> LOCATION: (3)...(4)
<223> OTHER INFORMATION: Positions 3-4 are mutated.

<400> SEQUENCE: 14
ugaacucuuu uu                                                              12

<210> SEQ ID NO 15
<211> LENGTH: 12
<212> TYPE: RNA
<213> ORGANISM: Homo sapiens
<220> FEATURE:
<221> NAME/KEY: variation
<222> LOCATION: (5)...(6)
<223> OTHER INFORMATION: Positions 5-6 are mutated.

<400> SEQUENCE: 15
uguuaacuuu uu                                                              12

<210> SEQ ID NO 16
<211> LENGTH: 12
<212> TYPE: RNA
<213> ORGANISM: Homo sapiens
<220> FEATURE:
<221> NAME/KEY: variation
<222> LOCATION: (7)...(8)
<223> OTHER INFORMATION: Positions 7-8 are mutated.

<400> SEQUENCE: 16
uguucuaauu uu                                                              12
```

```
<210> SEQ ID NO 17
<211> LENGTH: 12
<212> TYPE: RNA
<213> ORGANISM: Homo sapiens
<220> FEATURE:
<221> NAME/KEY: variation
<222> LOCATION: (9)...(10)
<223> OTHER INFORMATION: Positions 9-10 are mutated.

<400> SEQUENCE: 17
uguucucuaa uu                                                          12

<210> SEQ ID NO 18
<211> LENGTH: 12
<212> TYPE: RNA
<213> ORGANISM: Homo sapiens
<220> FEATURE:
<221> NAME/KEY: variation
<222> LOCATION: (11)...(12)
<223> OTHER INFORMATION: Positions 11-12 are mutated.

<400> SEQUENCE: 18
uguucucuuu aa                                                          12

<210> SEQ ID NO 19
<211> LENGTH: 268
<212> TYPE: DNA
<213> ORGANISM: Homo sapiens

<400> SEQUENCE: 19
tattctgcct gcttaaatat tactttcctc aaaaagagaa acaaaaatg ctagatttta        60 ctttatgact tgaatgatgt ggtaatgtcg aactctagta tttagaatta gaatgtttct      120
tagcggtcgt gtagttattt ttatgtcata agtggataat ttgttagctc ctataacaaa     180
agtctgttgc ttgtgtttca catttggat ttcctaatat aatgttctct ttttagaaaa       240
ggtggacaag tcctattttc aagagaag                                         268

<210> SEQ ID NO 20
<211> LENGTH: 267
<212> TYPE: DNA
<213> ORGANISM: Mus musculus

<400> SEQUENCE: 20
atgtgtttgg cattatgtga agcccaaaca ctaaaaaagg agaacaaaca aaagcgcaga       60
ctttaaaact caagtggttt ggtaatgtac gactctactg tttagaatta aaatgtgtct     120
tagttattgt gccattattt ttatgtcatc actggataat atattagtgc ttagtatcag     180
aaatagtcct tatgctttgt gttttgaagt tcctaatgca atgttctctt tctagaaaag     240
gtggacaagt cctattttcc agagaag                                          267

<210> SEQ ID NO 21
<211> LENGTH: 163
<212> TYPE: DNA
<213> ORGANISM: Homo sapiens

<400> SEQUENCE: 21
aattagaatg tttcttagcg gtcgtgtagt tattttatg tcataagtgg ataatttgtt        60
agctcctata acaaaagtct gttgcttgtg tttcacattt tggatttcct aatataatgt     120
tctcttttta gaaaaggtgg acaagtccta ttttcaagag aag                        163
```

<210> SEQ ID NO 22
<211> LENGTH: 162
<212> TYPE: DNA
<213> ORGANISM: Mus musculus

<400> SEQUENCE: 22
aattaaaatg tgtcttagtt attgtgccat tatttttatg tcatcactgg ataatatatt      60
agtgcttagt atcagaaata gtccttatgc tttgtgtttt gaagttccta atgcaatgtt     120
ctctttctag aaaaggtgga caagtcctat tttccagaga ag                        162

<210> SEQ ID NO 23
<211> LENGTH: 103
<212> TYPE: DNA
<213> ORGANISM: Homo sapiens

<400> SEQUENCE: 23
agctcctata caaaagtct gttgcttgtg tttcacattt tggatttcct aatataatgt       60 tctctttta gaaaggtgg acaagtccta ttttcaagag aag                         103

<210> SEQ ID NO 24
<211> LENGTH: 102
<212> TYPE: DNA
<213> ORGANISM: Mus musculus

<400> SEQUENCE: 24
agtgcttagt atcagaaata gtccttatgc tttgtgtttt gaagttccta atgcaatgtt      60
ctctttctag aaaaggtgga caagtcctat tttccagaga ag                        102

<210> SEQ ID NO 25
<211> LENGTH: 83
<212> TYPE: DNA
<213> ORGANISM: Homo sapiens

<400> SEQUENCE: 25
gttgcttgtg tttcacattt tggatttcct aatataatgt tctctttta gaaaaggtgg       60 acaagtccta ttttcaagag aag                                              83

<210> SEQ ID NO 26
<211> LENGTH: 83
<212> TYPE: DNA
<213> ORGANISM: Mus musculus

<400> SEQUENCE: 26
agtccttatg ctttgtgttt tgaagttcct aatgcaatgt tctctttcta gaaaaggtgg      60
acaagtccta ttttccagag aag                                              83

<210> SEQ ID NO 27
<211> LENGTH: 129
<212> TYPE: DNA
<213> ORGANISM: Homo sapiens

<400> SEQUENCE: 27
aattagaatg tttcttagcg gtcgtgtagt tattttatg tcataagtgg ataatttgtt       60
agctcctata caaaagtct gttgcttgtg tttcacattt tggatttcct aatataatgt     120
tctctttt                                                             129

<210> SEQ ID NO 28
<211> LENGTH: 128

-continued

```
<212> TYPE: DNA
<213> ORGANISM: Mus musculus

<400> SEQUENCE: 28
aattaaaatg tgtcttagtt attgtgccat tatttttatg tcatcactgg ataatatatt      60
agtgcttagt atcagaaata gtccttatgc tttgtgtttt gaagttccta atgcaatgtt     120
ctctttct                                                             128

<210> SEQ ID NO 29
<211> LENGTH: 234
<212> TYPE: DNA
<213> ORGANISM: Homo sapiens

<400> SEQUENCE: 29
tattctgcct gcttaaatat tactttcctc aaaaagagaa aacaaaaatg ctagatttta      60
ctttatgact tgaatgatgt ggtaatgtcg aactctagta tttagaatta gaatgtttct     120
tagcggtcgt gtagttattt ttatgtcata agtggataat ttgttagctc ctataacaaa     180
agtctgttgc ttgtgtttca cattttggat ttcctaatat aatgttctct tttt           234

<210> SEQ ID NO 30
<211> LENGTH: 233
<212> TYPE: DNA
<213> ORGANISM: Mus musculus

<400> SEQUENCE: 30
atgtgtttgg cattatgtga agcccaaaca ctaaaaaagg agaacaaaca aaagcgcaga      60
ctttaaaact caagtggttt ggtaatgtac gactctactg tttagaatta aaatgtgtct     120
tagttattgt gccattattt ttatgtcatc actggataat atattagtgc ttagtatcag     180
aaatagtcct tatgctttgt gttttgaagt tcctaatgca atgttctctt tct            233
```